United States Patent
Fujino et al.

(10) Patent No.: US 6,255,127 B1
(45) Date of Patent: Jul. 3, 2001

(54) ANALYZING METHOD AND APPARATUS FOR MINUTE FOREIGN SUBSTANCES, AND MANUFACTURING METHODS FOR MANUFACTURING SEMICONDUCTOR DEVICE AND LIQUID CRYSTAL DISPLAY DEVICE USING THE SAME

(75) Inventors: Naohiko Fujino; Isamu Karino; Masashi Ohmori, all of Hyogo; Masatoshi Yasutake; Shigeru Wakiyama, both of Chiba, all of (JP)

(73) Assignees: Seiko Instruments Inc., Chiba; Mitsubishi Denki Kabushiki Kaisha, Amagasaki, both of (JP)

( * ) Notice: Subject to any disclaimer, the term of this patent is extended or adjusted under 35 U.S.C. 154(b) by 0 days.

(21) Appl. No.: 09/187,938

(22) Filed: Nov. 6, 1998

Related U.S. Application Data

(62) Division of application No. 08/600,141, filed on Feb. 12, 1996, now Pat. No. 5,877,035.

(30) Foreign Application Priority Data

Feb. 14, 1995 (JP) .................................................... 7-025118

(51) Int. Cl.⁷ ............................ H01L 31/26; H01L 21/66
(52) U.S. Cl. ............................ 438/16; 438/18; 438/706; 250/234; 250/306; 250/307; 250/310
(58) Field of Search ................................ 438/16, 18, 706; 250/234, 306, 307, 310

(56) References Cited

U.S. PATENT DOCUMENTS 5,233,191 * 8/1993 Noguchi et al. .

(List continued on next page.)

FOREIGN PATENT DOCUMENTS 0633450    1/1995    (EP) .

(List continued on next page.)

OTHER PUBLICATIONS

Office Action of Japanese patent application No. 7–025118, mailed Feb. 10, 1998 from the Japanese Patent Office.

(List continued on next page.)

*Primary Examiner*—Kevin M. Picardat
*Assistant Examiner*—D. M. Collins
(74) *Attorney, Agent, or Firm*—Hogan & Hartson L.L.P.

(57) ABSTRACT

To enable observation, analysis and evaluation of minute foreign substances by adopting a method for enabling performance of linkage between equipment coordinates of a particle examination equipment and apparatus coordinates of an analyzing apparatus such as SEM which is not a particle examination equipment with a precision higher than that with which coordinate linkage is performed between conventional equipment and apparatus coordinates. An analyzing method for analyzing minute foreign substances comprises the steps of determining the position of a minute foreign substance on the surface of a sample in a particle examination equipment, transferring the sample to a coordinate stage of an analyzing apparatus and inputting the position of the minute foreign substance determined by the particle examination equipment to thereby analyze the contents of this minute foreign substance. It is characterized by linking the equipment coordinates adopted by the particle examination equipment with the apparatus coordinates adopted by the analyzing apparatus by use of the same coordinate system based on the configurations of the sample.

10 Claims, 8 Drawing Sheets

U.S. PATENT DOCUMENTS

| | | |
|---|---|---|
| 5,267,017 | 11/1993 | Uritsky et al. . |
| 5,274,434 | 12/1993 | Morioka et al. . |

FOREIGN PATENT DOCUMENTS

| | | |
|---|---|---|
| 0641021 | 3/1995 | (EP) . |
| 60-218845 | 11/1985 | (JP) . |
| 62-63646 | 11/1987 | (JP) . |
| 3156947 | 7/1991 | (JP) . |
| 3181848 | 8/1991 | (JP) . |
| 4123454 | 4/1992 | (JP) . |
| 6162987 | 6/1994 | (JP) . |
| 6317536 | 11/1994 | (JP) . |
| 6324003 | 11/1994 | (JP) . |
| 75407 | 1/1995 | (JP) . |

OTHER PUBLICATIONS

European search report dated Jan. 16, 1998, European patent application No. EPP11825A.

T. Hattori et al., "An Automated Particle Detection and Identification System in VLSI Wafer Processing," *Solid State Technology*, vol. 34, No. 9, Sep. 1991, pp. S01–S06.

* cited by examiner

ANALYZING METHOD AND APPARATUS FOR MINUTE FOREIGN SUBSTANCES, AND MANUFACTURING METHODS FOR MANUFACTURING SEMICONDUCTOR DEVICE AND LIQUID CRYSTAL DISPLAY DEVICE USING THE SAME

This is a division application of application Ser. No. 08/600,141 filed on Feb. 12, 1996, now allowed, Now U.S. Pat. No. 5,877,035.

BACKGROUND OF THE INVENTION

The present invention relates to an analyzing method for analyzing minute foreign substances existing on the surface of a planar sample such as a silicon wafer for use in manufacture of a semiconductor device, an insulative transparent substrate for use in manufacture of a liquid crystal display device, etc., an analyzing apparatus therefor, and a manufacturing method for manufacturing a semiconductor device or liquid crystal display device by using the analyzing method and analyzing apparatus. More particularly, the invention relates to a method and apparatus for, concerning a minute foreign substance having beedetected and having had its position particularized by a particle examination equipment whose equipment coordinates are defined beforehand, enabling easy analysis, examination and evaluation of the particularized minute foreign substance by linking the particularized existing position of the minute foreign substance with the coordinates of an analyzing apparatus, and a manufacturing method for manufacturing a semiconductor device and liquid crystal display device by using these method and apparatus.

Note the following. The analyzing apparatus referred to here in this specification is defined to mean an analyzing apparatus which irradiates energy of various corpuscular rays such as light, x rays, electromagnetic waves, electrons, neutral chemical species (atoms, molecules, etc.), ions or phonons onto the surface of a sample and detects secondary corpuscular rays absorbed or radiated due to interaction thereof with the sample to thereby examine the color tone, cubic image, elemental analysis, chemical structure, crystalline structure and the like of the surface of the sample or process this sample surface. For example, it includes apparatuses having the analyzing, examining, evaluating, and/or processing function such as, for example, metallurgical microscopes, laser microscopes, probe microscopes, interatomic force microscopes (hereinafter referred to as "AFM"), scanning tunnel microscopes (hereinafter referred to as "STM"), magnetic force microscopes (hereinafter referred to as "MFM"), scanning electron microscopes (Scanning Electron Microscope, hereinafter referred to as "SEM"), electron probe micro-analyzers (Electron Probe Micro-Analyzers, hereinafter referred to as "EPMA"), x-ray photoelectron spectrometers (X-ray Photoelectron Spectrometer, hereinafter referred to as "XPS"), ultraviolet photoelectron spectrometers (Ultraviolet Photoelectron Spectrometer, hereinafter referred to as "UPS"), secondary ion mass spectrometers (Secondary Ion Mass Spectrometer, hereinafter referred to as "SIMS"), time of flight-SIMSes (Time Of Flight-SIMS, hereinafter referred to as "TOF-SIMS"), scanning Auger electron spectrometers (Scanning Auger Electron Spectrometer, hereinafter referred to as "SAM"), Auger electron spectrometers (Auger Electron Spectrometer, hereinafter referred to as "AES"), reflection high energy electron diffraction spectrometers (Reflection High Energy Electron Diffraction Spectrometer, hereinafter referred to as "RHEED"), high energy electron diffraction spectrometers (High Energy Electron Diffraction Spectrometer, hereinafter referred to as "HEED"), low energy electron diffraction spectrometers (Low Energy Electron Diffraction Spectrometer, hereinafter referred to as "LEED"), electron energy-loss spectrometers (Electron Energy-Loss Spectrometer, hereinafter referred to as "EELS"), focused ion beam instruments (Focused Ion Beam Instruments, hereinafter referred to as "FIB"), particle induced X-ray emission spectrometers (Particle Induced X-Ray Emission, hereinafter referred to as "PIXE"), Microscopic Fourier transformation infrared-ray spectrometers (hereinafter referred to as "Microscopic FT-IR") or Microscopic Raman, observation apparatuses, analyzing apparatuses, examination apparatuses and evaluation apparatuses, having the above-mentioned functions.

It is said that inferior yield in the manufacture of ultrahigh LSIs represented by 4 M bit-DRAMs, 16 M bit-DRAMs and the like is for the most part attributable to defective wafers resulting from attachments on wafers.

The reason for this is that as the pattern width becomes micronized, a micro-size of foreign substances attached on wafers, which were conventionally not deemed as problematic, become contamination sources in preceding manufacturing process steps. Generally, it is said that the size of these problematic minute foreign substances is one of several of a minimum wiring width of an ultrahigh LSI to be manufactured. For this reason, in a 16 M bit-DRAM (minimum wiring width: 0.5 $\mu$m), minute foreign substances having a diameter of 0.1 $\mu$m or so are object foreign substances. These minute foreign substances become contamination substances which cause wiring breakage and shortcircuiting of the circuit patterns, which in turn largely causes generation of defective products and causes a decrease in the quality and reliability. Therefore, grasping the actual condition of minute foreign substances such as a state of attachment thereof through quantitative and precise measurement and analysis and conducting relevant managements are a key to increasing the yield.

As means for conducting the above-mentioned grasp and management, there is conventionally employed a particle examination equipment capable of detecting the positions of minute foreign substances existing on the surface of a planar sample such as a silicon wafer. Note that as the conventional particle examination equipments there are one produced by Hitachi Electron Engineering Limited and having an equipment name of IS-2000 and LS-6000, one produced by Tencor Corporation in the United States of America and having an equipment name of Surfscan 6200, one produced by Estek Corporation in the United States of America and having an equipment name of WIS-9000, and the like. Also, the measuring principles used in these particle examination equipments and the equipment constructions for realizing them are described in detail in, for example, a literature "High Performance Semiconductor Process Analysis and Evaluation Technology", pages 111 to 129, edited by Semiconductor Foundation Technology Study Association and published by Realize Ltd.

FIG. 9 illustrates a CRT display image screen which shows the results of measurements made on minute foreign substances (0.1 $\mu$m or more) existing on an actual 6-inch silicon wafer by using the particle examination equipment LS-6000. Namely, this display image screen only shows rough positions of minute foreign substances, the number thereof per unit size thereof and particle size distribution thereof. The circle shown in FIG. 9 indicates the outer periphery of the 6-inch silicon wafer and the dots existing therewithin correspond to the positions where minute foreign substances exist. Note that the particles and foreign substances described here are defined to mean foreign or different portions as viewed with respect to a wafer, such as protrusions, depressions, attaching particles, defects and the like, namely foreign or different portions at which light scattering (irregular reflection) occurs.

However, as seen from FIG. 9, since data obtained from conventional particle examination equipments are only the sizes of minute foreign substances existing on the surface of a sample such as a silicon wafer and the existence positions thereof on the sample surface, the actual condition of such minute foreign substances such as what these substances are cannot be particularized.

For example, FIG. 5 is a view illustrating a fundamental construction of a conventional actuator-equipped metallurgical microscope such as an IC examination microscope apparatus MODER: IM-120 put on sale from Nidek Co.Ltd., which is an example of a metallurgical microscope having the positioning function used for detecting minute foreign substances. In FIG. 5, a silicon wafer 2 as a sample is placed on an x-y actuator 1 having coordinates which have been roughly linked with the coordinates of a particle examination equipment. It is arranged that a foreign substance 7 detected by the particle examination equipment is carried into a view field of the metallurgical microscope 3 or into therearound on the basis of position data of the foreign substance obtained from the particle examination equipment by means of an x-y actuator 1. The examination procedures used when the foreign substance 7 existing on the surface of a planar silicon wafer is examined using a conventional actuator-equipped metallurgical microscope and the results of the examination will now be described.

First, a plurality of somewhat stained and mirror surface-polished silicon wafers 2 (Mitsubishi Material Silicon-Produced CZ <plane orientation: 100>6-inch diameter silicon wafer) were applied onto a particle examination equipment (a particle examination equipment produced by the United States of America, Tencor Corporation and having an equipment name of Surfscan 6200) and the rough sizes and rough existence positions of foreign substances existing on each silicon wafer 2 were observed. On each silicon wafer 2 there existed at random positions about 800 foreign substances whose sizes were in a range of from 0.1 to 0.2 $\mu$m in average, about 130 foreign substances whose sizes were in a range of from 0.2 to 0.3 $\mu$m in average, about 30 foreign substances whose sizes were in a range of from 0.3 to 0.4 $\mu$m in average, about 13 foreign substances whose sizes were in a range of from 0.4 to 0.5 $\mu$m in average, and about 15 foreign substances whose sizes were 0.5 $\mu$m or more. Note that the coordinates of the Surfscan 6200 are defined such that the direction of a straight line tangential to an orientation flat (hereinafter referred to as "an orientation flat") of the wafer is set to be an x coordinate axis (or y coordinate axis); the direction of a straight line perpendicular thereto within a wafer plane is set to be a y coordinate axis (or x coordinate axis); and three or more points on the outermost periphery of the wafer (however excluding the orientation flat portion) are measured and these points are applied to the equation of a circle or ellipse to thereby set the coordinates of the position of a center of the wafer to be (0, 0).

Next, using a conventional actuator-equipped metallurgical microscope, the direction of a straight line tangential to an orientation flat of the wafer is set to be an x coordinate axis; the direction of a straight line perpendicular thereto within a wafer plane is set to be a y coordinate axis (or x coordinate axis); and three or more points on the outermost periphery of the wafer (however excluding the orientation flat portion) are measured and these points are applied to the equation of a circle or ellipse to thereby set the coordinates of the position of a center of the wafer to be (0, 0). In this condition, the silicon wafer 2 was set on an x-y actuator 1 which, in turn, was moved according to the position data of the foreign substances obtained from the particle examination equipment. Thereafter, the foreign substances having their respective sizes were observed using the metallurgical microscope 3 (Note that the foreign substances were evaluated and observed with the ocular lens being set to fixed 20 magnifications and the objective lens being set to variable 5, 20 and 50 magnifications.)

As a result, in the case of using the metallurgical microscope with 5-magnification objective lens, it was only possible to observe foreign substances having a size of around 0.4 to 0.5 $\mu$m as dark dots at most and foreign substances having a size smaller than this size were almost not observed. On the other hand, foreign substances having: a size of 0.4 $\mu$m or more could all be observed. Meanwhile, in the case of using the 50-magnification objective lens, it was sometimes possible to observe foreign substances having a size of around 0.2 to 0.3 $\mu$m as dark dots. However, foreign substances having a size smaller than this size were almost not observed. Therefore, in order to investigate causes thereof, the amount of divergence between the coordinates at this time was examined using a plurality of wafers formed with grated patterns. As a result, it was proved that in the x-y coordinate display the amount of divergence of ($\pm 250$ $\mu$m, $\pm 250$ $\mu$m) in approximation existed regarding the origin position or center position and a given point definable therein.

In contrast, whereas the view field of the apparatus with 5-magnification objective lens, used at this time, was approximately 1500 $\mu$m$\Phi$, the view field of this apparatus with 50-magnification objective lens was only approximately 150 $\mu$m$\Phi$.

Namely, it was proved that the reason why at a time of the 50-magnification objective lens most of foreign substances having a-size of around 0.2 to 0.3 $\mu$m could not be found was that by changing the magnification of the objective lens from 5 magnifications to 50 magnifications the amount of divergence became larger than the range of the view field of the microscope, with the result that the object foreign substances having a size of around 0.2 to 0.3 $\mu$m did not fall within the view field of the presently available apparatus.

Accordingly, it is necessary to identify the actual condition of each of the individual minute foreign substances by directly observing or making composition analysis of these substances byluse of a suitable analyzing apparatus such as SEM. However, since the existence positions of individual foreign substances on the wafer obtained from the particle examination equipment are defined in the equipment coordinates of the particle examination equipment, those existence positions as defined therein are not always in coincidence with those defined in the apparatus coordinates of an analyzing apparatus which is not a particle examination equipment. Also, when a sample such as a wafer having had their foreign substances examined by the particle examination equipment is set on an analyzing apparatus such as SEM which is not a particle examination equipment, it is inevitable that coordinate divergence errors attributable to such new setting occur. For this reason, in order to identify the actual condition of a minute foreign substance, it is necessary to link the equipment coordinates of the particle examination equipment with the apparatus coordinates of an analyzing apparatus such as SEM which is not a particle examination equipment with a high precision by use of some measures.

Therefore, examination was performed on the equipment and apparatus coordinates on respective x-y stages of individual particle examination equipments and analyzing apparatuses such as SEM which are not particle examination equipments. As a result, it was found out that the coordinates on each of the x-y stages adopted in almost all of the equipments and apparatuses were of an x-y coordinate system. Also, the following two methods are adopted as methods for determining the coordinate axes and the origin position of each equipment or apparatus with respect to a wafer as a sample: (1) the direction of a straight line tangential to an orientation flat of the wafer is set to be an x coordinate axis (or y coordinate axis); the direction of a straight line perpendicular thereto within a wafer plane is set to be a y coordinate axis (or x coordinate axis); and a point of intersection between the outermost periphery of the wafer and the y coordinate axis is set to be (0, y) and a point of intersection between the y coordinate axis and the x coordinate axis is set to be (0, 0) (see FIG. 10($a$)), and (2) the direction of a straight line tangential to an orientation flat of the wafer is set to be an x coordinate axis (or y coordinate axis); the direction of a straight line perpendicular thereto within a wafer plane is set to be a y coordinate axis (or x coordinate axis); and three or more sampling points on the outermost periphery of the wafer are measured and these points are applied to the equation of a circle or ellipse to thereby set the coordinates of the position of a center of the wafer to be the origin (0, 0) (see FIG. 10 ($b$)).

However, in the above-mentioned methods, since the function used to define the coordinates or the number of sampling points differs according to the type of the equipments or apparatuses, the defined coordinate system also differs. Also, it is inevitable that the positions of sampling points become varying due to a difference in surface precision between the orientation flats or the outermost peripheral portions of wafers, due to a delicate difference in size between wafers, due to a difference in precision between the settings of wafers on the sample stage, or due to delicate warpage of a wafer. For this reason, divergence inevitably occurs between wafers or settings thereof in respect of the coordinate axis and the origin or center position. As a result of this, in a case where there is used a simple "method for linking coordinates which consists of inputting the position data of minute defects or foreign substances detected by a particle examination equipment to the coordinates of an analyzing apparatus which is not a particle examination equipment", which method was conventionally used, it is inevitable that divergence occurs between the equipment and apparatus coordinates with respect to each wafer in respect of the coordinate axis and origin. As a result, even when the analyzing apparatus is set to a magnification capable of analyzing minute foreign substances, it becomes impossible to set minute defects or foreign substances within a view field of that analyzing apparatus. For this reason, using a plurality of wafers formed with grated patterns, various equipments and apparatuses were examined concerning the amounts of divergence between their coordinates occurring due to the above-mentioned causes. As a result, it has been proved that even between high precision equipment and apparatus (a particle examination equipment produced by Hitachi Electron Engineering Limited and having an equipment name of IS-2000 and a length-measuring SEM produced by Hitachi Limited and having an apparatus name of S-7000) an amount of divergence of approximately (±100 $\mu$m, ±100 $\mu$m) occurs in the x-y coordinate display in respect of the origin position or center position and a given point definable therein. When it is desired to observe, analyze and evaluate a minute foreign substance at a given position on a wafer detected by a particle examination equipment by use of an analyzing apparatus such as SEM which is not a particle examination equipment, it becomes necessary to observe it at least within a range covering an area which spreads (±100 $\mu$m, ±100 $\mu$m) or more from a position where the minute foreign substance detected by the particle examination equipment is considered to exist, taken as the center (200 $\mu$m×200 $\mu$m=40000 $\mu$m, the view field of SEM having 500 magnifications), by use of an analyzing apparatus such as SEM which is not a particle examination equipment and thereby confirm the position of it, and then conduct observation, analysis and evaluation thereof which are the initial goal by some suitable method such as by enlargement thereof. This requires the use of a significantly long period of time.

On the assumption that in order to intuitionally grasp of what size this range is with respect to a minute foreign substance this range of 40000 $\mu$m$^2$ (200 $\mu$m×200 $\mu$m) has been observed using a 1-million pixel CCD camera presently considered as a CCD camera having a relatively high resolving power, the minimum size of a minute foreign substance considered as being detectable attempts to be considered by calculating a detection range (area) occupied by one pixel of this CCD camera. The detection range occupied by one pixel under the above-mentioned conditions is calculated to be 0.04 $\mu$m$^2$ (4 million $\mu$m$^2$÷1 million= 0.2 $\mu$m×0.2 $\mu$m). On the other hand, since a substance having a size smaller than the size corresponding to the one-pixel detection range is difficult to discriminate, the minimum detectable size of a minute foreign substance is 0.04 $\mu$m$^2$ (0.2 $\mu$m×0.2 $\mu$m). Namely, it is difficult to detect a minute foreign substance whose projection area is smaller than 0.04 $\mu$m$^2$ (the diameter: 0.2 $\mu$m) by directly using a 1-million pixel CCD camera. It is also seen that it is very difficult to particularize the position of the minute foreign substance. To say furthermore, it is almost impossible to particularize the position of a minute foreign substance having a size of 0.2 $\mu$m or less.

For the above-mentioned reasons, in the prior art, it is generally difficult to particularize the position of a minute foreign substance with a diameter of 0.2 $\mu$m or less detected by a particle examination equipment and directly observe or evaluate the minute foreign substance, by causing linkage between the equipment coordinates of the particle examination equipment and the apparatus coordinates of an analyzing apparatus such as SEM which is not a particle examination equipment.

Meanwhile, in order to cause the place where a foreign substance exists within a wafer to be interrelated between a foreign substance examination equipment and an analyzing apparatus, interface means is provided for storing and communizing position coordinate data of a detected minute foreign substance and also making file conversion and coordinate transformation. Then, the communized position coordinate data are used in each of the equipment and apparatus to thereby correct positional divergence between the equipment and the apparatus. This method of correcting is disclosed in Unexamined Japanese Patent Publication No. H-4-123454. Also, Unexamined Japanese Patent Publication No. H-3-102845 discloses a method of setting a coordinate system used as a standard with respect to wafers, providing each examination equipment with a conversion section for making conversion between the standard coordinate system and a coordinate system specific for the examination equipment, and inputting and outputting the coordinates totally in accordance with the standard coordinate system, or setting the coordinate system of each equipment totally in accordance with the standard coordinate system. However, in any one of these methods, a coordinate system specific for each equipment or a standard coordinate system is defined using a scribe line on a wafer or, for example, one leftmost point of a wafer periphery as a standard. Therefore, the resulting coordinate axis per se diverges due to the detection precision of the scribe line or orientation flat of a wafer or the leftmost point of a wafer periphery (which largely differs if the direction of the x coordinate axis is inclined even a little bit) and therefore is not an invariable coordinate axis. For this reason, it is inevitable that coordinate axis divergences occur between the equipments and apparatuses.

SUMMARY OF THE INVENTION

The present invention has been made in order to solve the above-mentioned problems and an object of the present invention is to provide an analyzing method for analyzing minute foreign substances which can observe, analyze and evaluate minute foreign substances by adopting a method enabling linkage between the equipment coordinates of a particle examination equipment and the apparatus coordinates of another analyzing apparatus such as SEM which is not a particle examination equipment with a precision higher than the precision of linkage performed between the equipments and apparatuses wherein conventional linkage methods are adopted.

Another object of the present invention is to provide a manufacturing method for manufacturing a semiconductor device or liquid crystal display device which enables an increase in the yield of a semiconductor device, liquid crystal display device or the like, as well as an increase in the reliability thereof, by examining and analyzing minute foreign substances on the surface of an insulative transparent substrate such as a wafer or glass in the manufacturing process steps thereof by use of the above-mentioned analyzing method.

An analyzing method for minute foreign substances according to the present invention comprises the steps of determining in a particle examination equipment the position of a minute foreign substance on the surface of a sample, transferring the sample onto a coordinate stage of an analyzing apparatus, and inputting to the analyzing apparatus the position of the minute foreign substance determined by the particle examination equipment to thereby analyze the contents of the minute foreign substances, and is characterized by further comprising a step of linking equipment coordinates adopted in the particle examination equipment with apparatus coordinates adopted in the analyzing apparatus by use of the same coordinate system determined based on configurations of the sample.

The coordinate system based on configurations of the sample is determined by measuring the positions of sampling points of predetermined portions of the sample reflecting an outer peripheral configuration thereof. This enables determination of the coordinate system with no errors.

The sample is a circular wafer having an orientation flat; at least three points of a circular portion of the wafer and at least two points of the orientation flat portion are measured as sampling points by using the equipment and apparatus coordinates of the particle examination equipment and analyzing apparatus; and the coordinates of a center of the circle of the sample and the inclination of the orientation flat are determined from the sampling points thus measured, whereby an x-y coordinate system wherein the direction of the inclination is set as an x coordinate axis or y coordinate axis and the coordinates of a center of the circle are set as those of the origin is used as the same coordinate system based on configurations of the sample.

Four or more points are selected as the sampling points from the circular portion and three or more points are selected as the sampling points from the orientation flat portion, whereby the coordinates of a center of the circle and the inclination of the orientation flat are determined from the measured coordinates of the sampling points by use of least square, thereby enabling linkage between respective coordinates of the equipment and apparatus with a higher precision.

It is preferable that the sampling points of the circular portion are set at positions on the outer peripheral portion taken at substantially equal intervals, because this enables a decrease in the error concerning the center coordinates.

The wafer may be a semiconductor element which is midway during a manufacturing process for manufacturing a semiconductor device, or a semiconductor wafer from which the semiconductor element is being manufactured.

The sample is an angular substrate; angular portions of the angular substrate are measured as sampling points by using the equipment and apparatus coordinates of the particle examination equipment and analyzing apparatus; and the coordinates of a center obtained from a point of intersection between vertical bisectors of prescribed two sides of the angular configuration and the inclination of a prescribed one side thereof are determined, whereby an x-y coordinate system wherein the direction of the inclination is set as an x coordinate axis or y coordinate axis and the coordinates of the center are set as those of the origin can be determined as the same coordinate system based on the sample.

In the analyzing method of the present invention the inclination of the prescribed one side can be determined by measuring sampling points other than the angular portions.

It is preferable that the inclination of the prescribed one side be determined by measuring three or more sampling points by use of least square, because this enables an increase in the precision of coordinate transformation.

The angular substrate may be a liquid crystal display element midway during a manufacturing process for manufacturing a liquid crystal display device, or an insulative transparent substrate from which the liquid crystal display element is being manufactured.

An analyzing apparatus for analyzing minute foreign substances is one for analyzing minute foreign substances comprising a stage on which there is placed a sample the position of whose minute foreign substance has been detected in a particle examination equipment to thereby analyze the minute foreign substance, and further comprises means for determining the inclination of at least one prescribed linear portion of the sample by use of apparatus coordinates of the analyzing apparatus, means for determining the coordinates of a center of the sample from sampling points on an outer periphery thereof by use of the apparatus coordinates, and coordinate transformation means for making coordinate transformation between a coordinate system determined based on the inclination and center coordinates and the apparatus coordinates.

The means for determining the center coordinates may be one which determines the center coordinates by calculation made on the assumption that the measured sampling points satisfy the equation of a circle.

The analyzing apparatus for the above-mentioned analyzing methods and analyzing apparatuses may be one selected from the group consisting of a scanning electron microscope, a metallurgical microscope, a scanning laser microscope, a Microscopic infrared spectrometer for analysis of a chemical structure, a Microscopic Raman spectrometer, a photoluminescence spectral analyzer for making fluorescence spectral analysis, an electron probe micro analyzer for making elemental analysis of a minute amount of surface elements, an Auger electron spectrometer, an electron energy-loss spectrometer, a secondary ion mass spectrometer, a time of flight-mass spectrometer, a particle induced-x-ray emission, a reflection high energy electron diffraction spectrometer for analysis of crystals, focused ion beam instruments for making surface process, an x-ray photoelectron spectrometer for making structural analysis, an ultraviolet photoelectron spectrometer for making composition analysis, a scanning probe microscope, an interatomic force microscope, a scanning tunnel microscope, and a magnetic force microscope.

The particle examination equipment according to the present invention is adapted for detecting minute foreign substances on a sample, and comprises means for determining the inclination of at least one prescribed linear portion of the sample by use of equipment coordinates of the particle equipment, means for determining the coordinates of a center of the sample from sampling points on an outer periphery thereof by use of the equipment coordinates, and coordinate transformation means for making coordinate transformation between a coordinate system determined based on the inclination and center coordinates and the equipment coordinates.

Also, the manufacturing method for manufacturing a semiconductor device according to the present invention is a process for manufacturing a semiconductor device which comprises at least a cleaning step, a film forming step, an exposure step, an etching step, an ion implantation step, a diffusion step and a heat treating step at least one of which includes an examination step at least one sub-step of which is intended for analyzing minute foreign substances by the method set forth in claim 1 or the apparatus set forth in another claim.

Furthermore, the manufacturing method for manufacturing a liquid crystal display device is one for manufacturing a liquid crystal display device comprising the steps of adhering a TFT substrate having an insulative transparent substrate provided with at least a thin film transistor and a pixel electrode to an opposing substrate having an insulative transparent substrate provided with at least an opposing electrode, at peripheries thereof with a prescribed gap therebetween, and injecting liquid crystal material into the gap, wherein at least one of a cleaning step, a film forming step, an exposure step, an etching step, and an ion implantation step which constitute a manufacturing process for manufacturing the TFT substrate or opposing substrate includes an examination step at least one sub-step of which is intended for analyzing minute foreign substances by the method set forth in claim 1 or the apparatus set forth in another claim.

According to the analyzing method for minute foreign substances as set forth in claim 1, since linkage between the equipment coordinates of the particle examination equipment and the apparatus coordinates of the analyzing apparatus is performed through the intermediary of a coordinate system based on configurations of the sample, it is possible to bring the both coordinates into corresponding relation to each other with a very high precision. As a result, it is possible to reliably set the rough position of a minute foreign substance detected by the particle examination equipment into the view field of the analyzing apparatus wih a high magnification in a short period of time and thereby analyze the minute foreign substance with high efficiency.

According to the analyzing method as set forth in claim 2, since a coordinate system for a sample is defined by reflecting the configuration of the outer peripheral portion thereof, namely by measuring the positions of sampling points of predetermined portions thereof, it is possible to reliably determine an accurate coordinate system with respect to even samples whose sizes are widely varying without the need to apply a mark to a sample or the like.

According to the analyzing method as set forth in another claim, in a case where the sample is a circular wafer having an orientation flat portion, since a coordinate system used as a standard is defined by determining the inclination of the straight line portion of the orientation flat portion and the center coordinates of the circle, it is possible to easily define a coordinate system based on configurations of the wafer.

According to the analyzing method as set forth in another claim, since many sampling points are selected, it is possible to correct errors due to deformation or the like of the wafer configuration and thereby determine the center coordinates of the true circle or the inclination of the orientation flat.

According to the analyzing method as set forth in another claim, since the equidistant points on the outer peripheral portion of the circular portion are selected as the sampling points, even when the circular portion is not a complete circle but is deformed into a slightly elliptic configuration, adverse effect upon determining the center coordinates becomes small and it is possible to make the error small.

According to the analyzing method as set forth in another claim, since it is possible to analyze a minute foreign substance on a semiconductor wafer midway during the manufacturing process therefor, it is possible to analyze causes of defects in the process of manufacturing a semiconductor device.

According to the analyzing method as set forth in another claim, even the sample is an angular substrate, it is possible to set a coordinate system based on the outer configuration thereof with a high precision.

According to the analyzing method as set forth in another claim, even when the sample is an angular substrate, it is possible to precisely determine the inclination of one side thereof.

According to the analyzing method as set forth in another claim, since it is possible to analyze a minute foreign substance on an insulative transparent substrate midway during a manufacturing process for manufacturing a liquid crystal display device, it is possible to analyze causes of defects in the course of this manufacturing process.

According to the method or apparatus as set forth in another claim, it is possible not only to analyze surface configuration, elemental analysis, chemical structure and crystalline structure of a minute foreign substance but also to perform surface processing by selecting the type of the analyzing apparatuses.

According to the analyzing apparatus as set forth in another claim, since means for determining a coordinate system based on configurations of a sample are provided, the position of a minute foreign substance roughly detected by a particle examination equipment provided with these means is accurately linked with the apparatus coordinates of the analyzing apparatus, whereby the minute foreign substance can be easily set within the view field of the analyzing apparatus.

According to the analyzing apparatus as set forth in another claim, when the sample is circular, the coordinates of the center position thereof can be reliably determined by using given three or more points on the circumference thereof as the sampling points. On the other hand, even when the outer configuration of the sample is not circular, particularization can be made at the same position in each of the particle examination equipment and analyzing apparatus by using a point of intersection between bisectors each obtained from prescribed two sides of the sample as the center coordinates, namely complete linkage of the equipment and apparatus coordinates between the equipment and apparatus becomes possible.

According to the particle examination equipment as set forth in another claim, since means for determining a coordinate system based on configurations of a sample is provided, it is possible to perform reliable linkage of the equipment and apparatus coordinates between the particle examination equipment and an analyzing apparatus provided with means for determining the same coordinate system.

According to the manufacturing method for manufacturing a semiconductor device as set forth in another claims, since the state of a minute foreign substance on the surface of a wafer can be picked up, or examined by total inspection, at any desired time in the mid course of the manufacturing process, it is possible to know the generated state or generated causes of the minute foreign substance during the manufacturing process and immediately feed them back to this manufacturing process. As a result, even in the case of an ultrahigh LSI with respect to which wiring of submicron order is imparted, it is possible to minimize the occurrence of inconveniences attributable to the minute foreign substance and thereby enhance the reliability as well as the yield.

Also, according to the manufacturing method for manufacturing a liquid crystal display device as set forth in another claims, since the state of a minute foreign substance can be understood in the mid course of the process for forming thin transistors, signal wirings or the like, it is possible to prevent occurrence of a trouble such as breakage even when the wiring of the liquid crystal display device is reduced in width as it becomes greatly micronized.

DETAILED DESCRIPTION OF THE INVENTION

Figure 1:
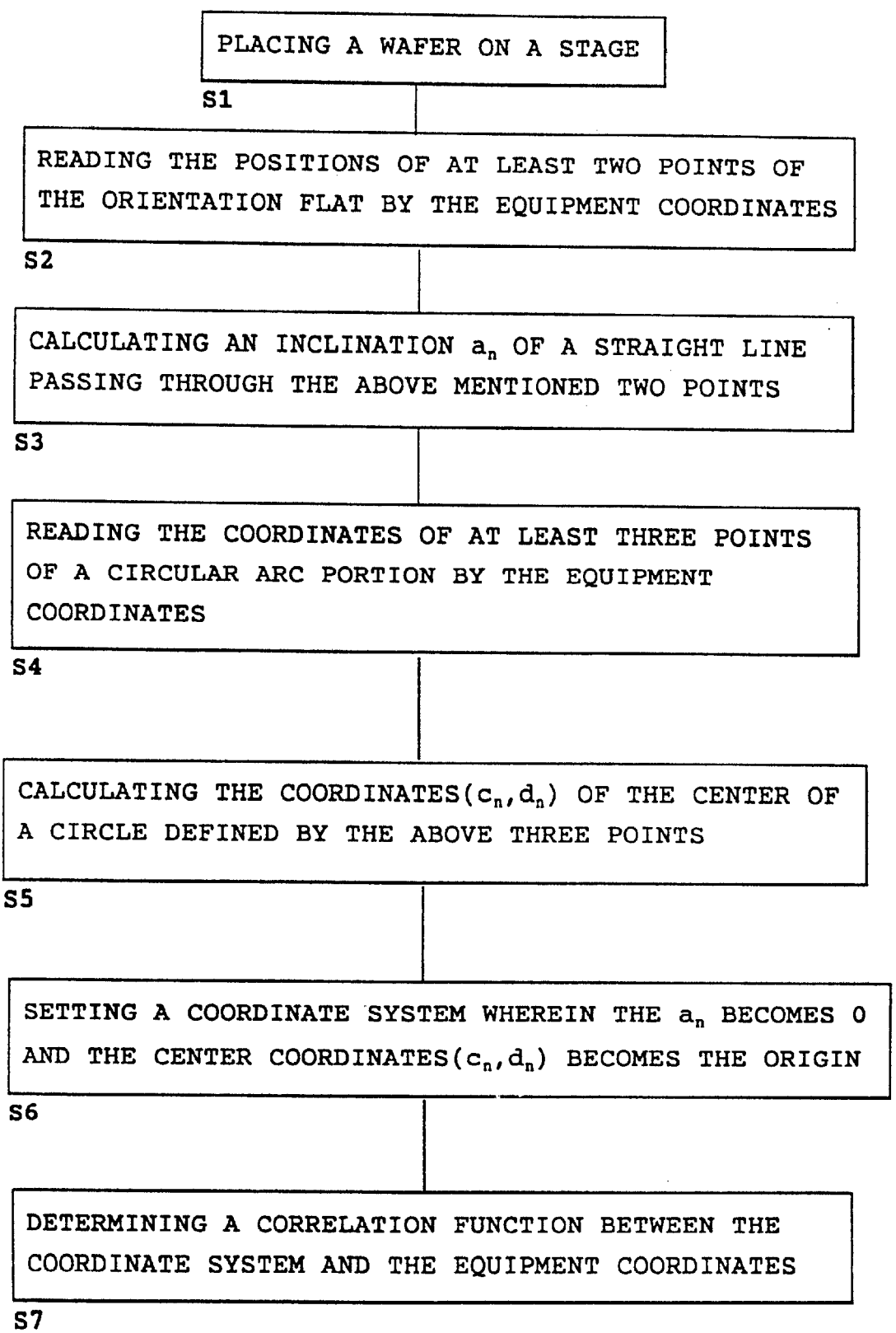
FIG. 1 is a flow chart for determining a correlation function between a common coordinate system based on configurations of a sample and equipment and apparatus coordinates in each of an analyzing method and analyzing apparatus of the present invention.

Next, an analyzing method for analyzing a minute foreign substance, an analyzing apparatus therefor, and a manufacturing method for manufacturing a semiconductor device or liquid crystal display device by use thereof, according to the present invention will be explained.

The analyzing method for analyzing a minute foreign substance according to the present invention is one which, when determining the position of a minute foreign substance on the surface of a sample by a particle examination equipment, transferring the sample onto a coordinate stage of an analyzing apparatus and determining in the coordinates of the analyzing apparatus the position of the minute foreign substance determined by the particle examination equipment, causes the respective equipment and apparatus coordinates of the particle examination equipment and analyzing apparatus to be linked with each other through the intermediary of the same coordinate system based on configurations of a sample. As a result, the minute foreign substance detected by the particle examination equipment can be easily positioned within the view field of the analyzing apparatus in corresponding relation to the position thereof in the particle examination equipment, thereby enabling simple performance of analyses of the surface configuration, elemental analysis, chemical structure, crystalline structure, etc. thereof.

As stated previously, it is very difficult and requires the use of a significantly long period of time to transfer, in order to further examine and analyze by an analyzing apparatus in which a conventional coordinate system is adopted a minute foreign substance detected by the particle examination equipment in which a conventional coordinate system is adopted, the sample such as a wafer to the analyzing apparatus and perform positioning of the minute foreign substance detected by the particle examination equipment within the view field of the analyzing apparatus. The present inventors have made their earnest repeated studies in order to enable easy positioning of a minute foreign substance detected by the particle examination equipment within the view field of the analyzing apparatus and as a result have found out that occurrence of positional divergence between the equipment and apparatus is due to a failure to obtain a coincidence between the position coordinates of a minute foreign substance on the sample such as a wafer particularized by the particle examination equipment and the position coordinates of the minute foreign substance on the sample particularized by a certain coordinate system of the analyzing apparatus. That is, even when some point on a sample is marked and the sample is set in each of the equipment and apparatus in the same manner by use of the marked point to thereby perform corresponding positioning in regard to each of the equipment coordinates and apparatus coordinates, divergence error becomes large, with the result that no complete coincidence is obtained. The present inventors have made their further earnest and repeated studies in order to obtain a coincidence between the position coordinates of the both equipment and apparatus and as a result have found out that it is possible to make the coordinate divergence error between the both equipment and apparatus very small by performing linkage between the coordinate systems of the both equipment and apparatus through the intermediary of the same invariable and fixed coordinate system based on configurations of a sample, thus completing the present invention. Furthermore, the present inventors have found out that if, when setting coordinate axes with respect to a sample, equidistant three or more points on the periphery thereof are selected as measuring points (sampling points) with respect thereto, it is possible to make the coordinate divergence error between the equipment and apparatus smaller.

[Embodiment No. 1]

As stated previously, in order to link the equipment coordinates of a particle examination equipment with the apparatus coordinates of an analyzing apparatus which is not a particle examination equipment, it is most advisable to define the equipment coordinates and apparatus coordinates adopted in the equipment and apparatus by use of the same definition formula. The reason for this is as follows. When the equipment coordinates and apparatus coordinates are defined respectively in the equipment and apparatus by use of different definition formulas, it becomes necessary to perform some coordinate transformation in the process of performing coordinate linkage and, at the time of performing this coordinate transformation, divergence error occurs. Also, the positions of the sampling points which are measuring points on a wafer as the sample from which the coordinate axes are determined differ according to the type of the definition formulas and, in addition, the sampling points necessary for definition also differ. As a result, the reference points on the outer periphery of the wafer which is microscopically not a complete circle differ, with the result that the origins of the coordinate axes do not completely coincide with each other. For this reason, the possibility that divergence error may occur when coordinate transformation is performed between the both equipment and apparatus becomes high.

First, selection is made of a coordinate system which is effective for linking different equipment and apparatus coordinates efficiently. Note here that it is very difficult to primarily define the position coordinates of a given position on a wafer which naturally is varying in size and configuration by applying only the equipment or apparatus coordinates with respect thereto without considering the configurations thereof. Therefore, by considering the configurations of wafers intended to be evaluated, coordinate systems are determined using points on individual wafers as references and one of these coordinate systems is determined by means of each of the equipment and apparatus coordinates specific for the equipment and apparatus. Thereby, the position coordinates of a given position on the wafer are absolutely defined. That is, a coordinate system based on the consideration of the configurations of individual wafers is set and the position coordinates of a given position on each of the individual wafers are defined in each of the equipment and apparatus. Next, a concrete method therefor will be explained with reference to a flow chart of FIG. 1.

In order to link the equipment coordinates of a particle examination equipment with the apparatus coordinates of an analyzing apparatus which is not a particle examination equipment with respect to a wafer which is varying in size and length of orientation flat with a high precision, a coordinate system which satisfies the following conditions is defined and set.

(1) The coordinate system defined on a wafer does not depend upon the size and length of orientation flat of the wafer.

(2) The coordinate system defined on a wafer is free from the influence of states of setting of the wafer.

It has been found out as a result of the studies that a coordinate system wherein the direction of the orientation flat of a wafer is set to be an x coordinate axis and the center defined from the outer periphery of the wafer is set to be the origin S is effective as the coordinate system Fa satisfying the above-mentioned conditions.

(a) First, a wafer is placed on a stage of a particle examination equipment and is scanned by laser beams, whereby the beam spots are irradiated thereonto. Then, the positions of at least two points $OP_{n1}$, $OP_{n2}$ (see FIG. 2) of the orientation flat portion of the wafer are read by the equipment coordinates $(x_t, y_t)$ of the particle examination equipment (see S1 and S2).

Next, an equation (the following equation (1)) for a straight line passing through the above-mentioned two points is determined to thereby calculate the inclination $a_n$ thereof (see S3).

$$Y_t = a_n X_t + b \quad (1)$$

Next, the beam spots of laser are irradiated onto a circular arc portion of the wafer which is not the orientation flat thereof, whereby the positions of at least three points $CP_{n1}$, $CP_{n2}$, and $CP_{n3}$ (see FIG. 2) are read by the equipment coordinates of the particle examination equipment (see S4).

Next, assuming that the above three points thus read take their positions on the circumference of a circle expressed by the following circle equation, the coordinates $(c_n, d_n)$ of the center thereof are calculated (see S5).

$$R^2 = (x_t - c_n)^2 + (y_t - d_n)^2 \quad (2)$$

Next, a coordinate system wherein the $a_n$ of the above equation (1) becomes 0 and the center coordinates $(c_n, d_n)$ of the equation (2) becomes the origin (0, 0) is set (see S6), and the correlation function between this coordinate system and the equipment coordinates is determined to thereby transform the equipment coordinates of the particle examination equipment to the coordinates of the coordinate system based on the configurations of the sample (see S7).

(b) Next, a wafer is placed on a stage of an analyzing apparatus and the same operation as that performed under the item (a) is repeated. At this time, in the analyzing apparatus, irradiation of the wafer by use of beam spots which is performed in the case of the particle examination equipment under the item (a) is not performed. For this reason, in the analyzing apparatus, the position of a wafer end, i.e., sampling points is recognized by observing the wafer by use of a microscope or the like. That is, the orientation flat portion or circular arc portion of the wafer is set within the view field of a microscope by a method such as that of scanning the wafer surface by the microscope to thereby recognize the sampling points and read the position thereof into the scanning coordinates. Note that since it is sufficient that the magnification of the microscope be low, the view field thereof can be set wide.

Then, a coordinate system wherein the direction tangential to the orientation flat is set to be an x coordinate axis (y coordinate axis) and the center of the circular arc portion of the wafer is set to be the origin is brought on the apparatus coordinates of the analyzing apparatus into corresponding relation (correlation function) thereto.

As a result, the equipment coordinates of the particle examination equipment and the apparatus coordinates of the analyzing apparatus are inter-related through the intermediary of the coordinate system determined based on the configurations of a wafer which is a sample. Transformation between the both coordinates which is performed in each of the equipment and apparatus through the above-mentioned series of operations to thereby cause interrelation between both the equipment and the apparatus is performed in each of computers thereof having the above-mentioned processing means. Also, by the correlation function being input to each of these computers, mere operating of it in the both equipment and apparatus by means of the equipment coordinates and apparatus coordinates enables procurement of more reliable interrelation than in the prior art and also enables a decrease in the positional divergence. Therefore, it is possible to set a more minute foreign substance detected by the particle examination equipment into the view field of the analyzing apparatus with a magnification capable of discriminating the minute foreign substance, thereby making it possible to particularize the position thereof in a shorter period of time.

When divergence error occurs between the equipment coordinates and apparatus coordinates of the both equipment and apparatus, it depends upon the respective precisions of the inclination an of a tangential direction to the orientation flat of a wafer used as a reference and the center coordinates $(c_n, d_n)$ of the circular arc portion thereof. However, since a coordinate system based on the configurations of a wafer as a sample is used with respect to both the particle examination equipment and the analyzing apparatus, it is possible to perform coordinate transformation between the both equipment and apparatus with a very high precision.

While in the above-mentioned embodiment the coordinate system based on the using of a tangential direction to the orientation flat of a wafer and the center of a circular arc portion thereof as a reference has been used as a transformation coordinate system, the center of the circular arc portion need not be used as the origin. Namely, the relation between the x coordinate axis and the y coordinate axis may be selected to be one between a tangential direction to the orientation flat and a direction perpendicular thereto, whereby the origin may be selected to be at another position. Also, it is not always necessary that the center of the circular arc portion be determined and the tangential direction to the orientation flat and the direction perpendicular thereto be determined. That is, the transformation coordinate system may be one using a relation between the leftmost or rightmost end of the circular arc portion and a direction perpendicular to the tangential direction to the orientation flat. However, as stated previously, preferably, the center of the circular arc portion is determined from three or more points thereof because this increases the precision.

Figure 3:
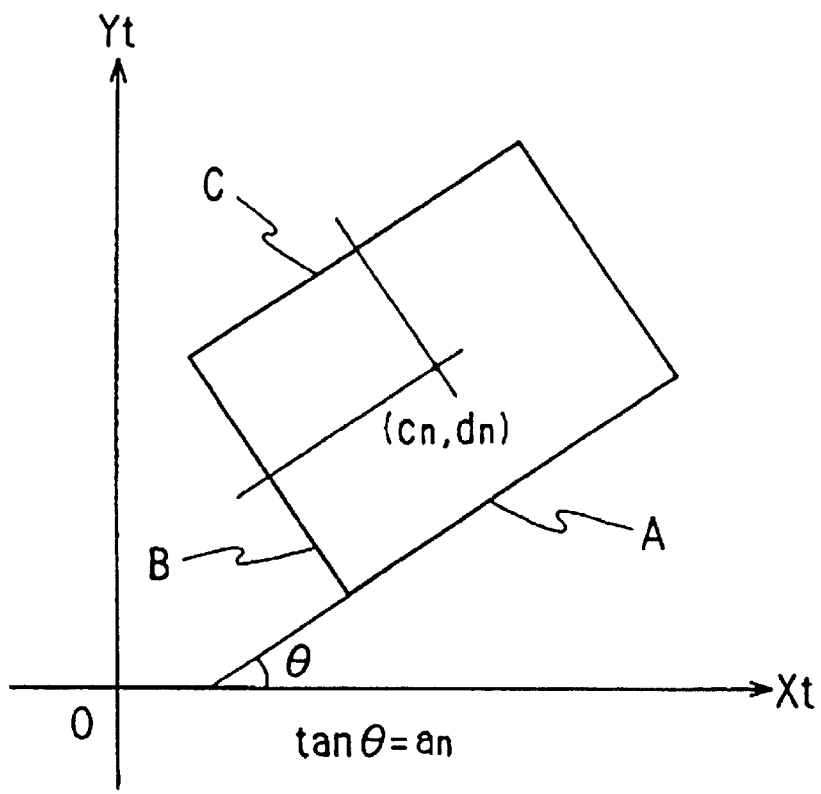
FIG. 3 is a view illustrating a method for defining the common coordinate system when a rectangular substrate has been placed as the sample.

Further, in the above-mentioned embodiment, the explanation thereof has been given using a silicon wafer for use in manufacture of a semiconductor device as an example. However, in the case of a rectangular material having no circular arc portion such as an insulative transparent substrate for use in manufacture of a liquid crystal display element, as illustrated in FIG. 3, one side A of the rectangular configuration is particularized and the inclination $a_n$ thereof is determined, and the coordinates of both ends of each of the other two sides B and C are detected, whereby the coordinates $(c_n, d_n)$ of the point of intersection between vertical bisectors thereof are used as a reference. Thereby, it is possible to perform coordinate transformation between the both equipment and apparatus through the intermediary of the coordinary system based on the particular configurations of a sample in the same manner as mentioned before.

[Embodiment No. 2]

In the embodiment no. 1, the equipment and apparatus coordinates adopted respectively in the particle examination equipment and the analyzing apparatus were defined with the use of the same coordinate system to thereby increase the precision with which the coordinate transformation was performed, thereby enabling direct transfer of a minute foreign substance detected by the particle examination equipment into the view field of the analyzing apparatus and enabling analysis thereof. In this embodiment, it is intended to further increase the precision of the coordinate transformation so that even when the magnification of the analyzing apparatus is increased up to several times or so higher, a minute foreign substance may be set from the equipment coordinates of the particle examination equipment more reliably into the apparatus coordinates of the analyzing apparatus, i.e., the view field thereof.

Figure 4A:
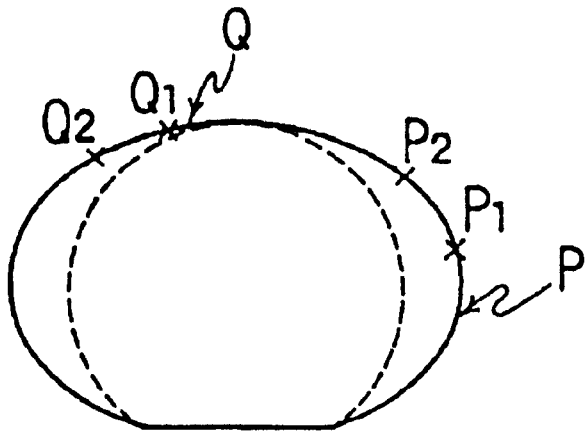
FIG. 4 is a view illustrating a state of deformation of the peripheral edge portion of a wafer on an enlarged scale.
Figure 4B:
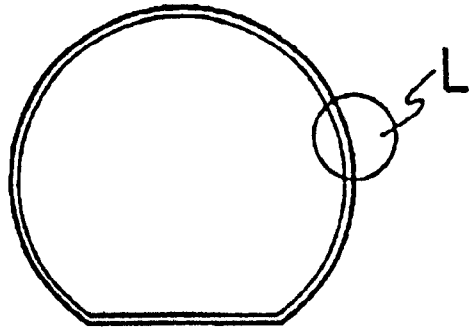

A silicon wafer for use in manufacture of a semiconductor device is formed into a circular arc configuration except for an orientation flat portion for indication of the crystalline direction, and the periphery thereof is polished. However, the wafer is formed with same semiconductor circuits in the form of crosses of the substrate and is diced horizontally and vertically, thus being formed into a square chip configuration. For this reason, the peripheral edge of the circular arc portion cannot be used as a chip and is discarded. Therefore, it is not always necessary that the outer periphery of the circular arc portion be a complete circle. Namely, although being macroscopically circular, the outer periphery microscopically is elliptic or has protrusions and depressions on its surface as illustrated in FIG. 4 (FIG. 4($c$) is an enlarged view of an L portion of FIG. 4($b$)). If the outer periphery of the wafer is a complete circle, by observing any three points on the outer periphery the center thereof can be reliably determined and this center is always a fixed point. However, unless the outer periphery is a complete true circle as mentioned above, divergence occurs in respect of the position of the center determined from the sampling three points. That is, divergence occurs between the position of a center of the wafer determined by the particle examination equipment and the position of a center of the wafer determined by the analyzing apparatus. As a result, there occurs, due to coordinate transformation between the equipment coordinates of the particle examination equipment and the apparatus coordinates of the analyzing apparatus, a case where the minute foreign substance detected by the particle examination equipment cannot reliably be set within the view field of the high-magnification analyzing apparatus.

As illustrated in FIG. 4($a$), in a case where the outer periphery of the wafer is, for example, elliptic in shape, when sampling points $P_1$ and $P_2$ of the outer periphery thereof whose radius of curvature is relatively small as indicated by P of FIG. 4($a$) or sampling points $Q_1$ and $Q_2$ of the outer periphery thereof whose radius of curvature is relatively large as indicated by Q are sampled two or three in number, divergence error becomes large.

Figure 4C:
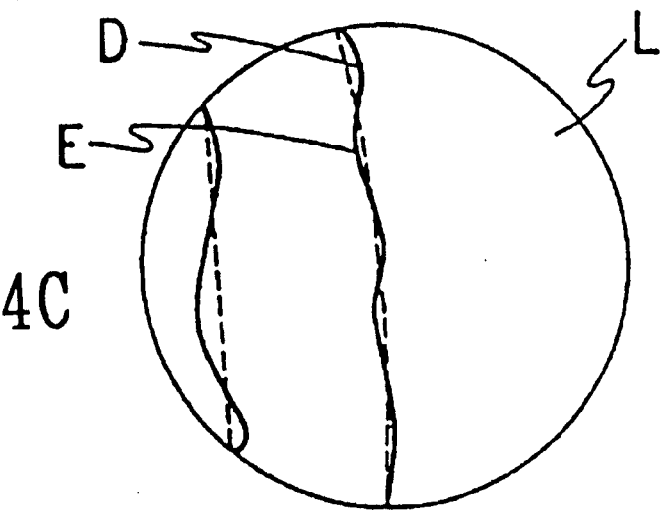

This embodiment is directed, from the viewpoint that even when the outer configuration of the wafer microscopically is not a true circle, it is a true circle in approximation as viewed macroscopically, to selecting three sampling points on the circular arc configuration for determining the center thereof at equally spaced positions so that these three sampling points may be approximately equally distant from each other and performing relevant measurements. As a result of this, even if the measuring points are different points on the circumference, mutual relation between these three points become the same, with the result that a substantially fixed set of coordinates can be obtained as the center coordinates to be determined. Also, as illustrated in FIG. 4(c) as the enlarged view of the outer peripheral portion, where the outer configuration thereof has protrusions or depressions, when sampling points are set at positions relatively near to each other which are indicated by D and E of FIG. 4(c), the influence of these protrusions or depressions comes out. However, this influence can be mitigated by selecting the three points at, for example, equally spaced positions.

Figure 2:
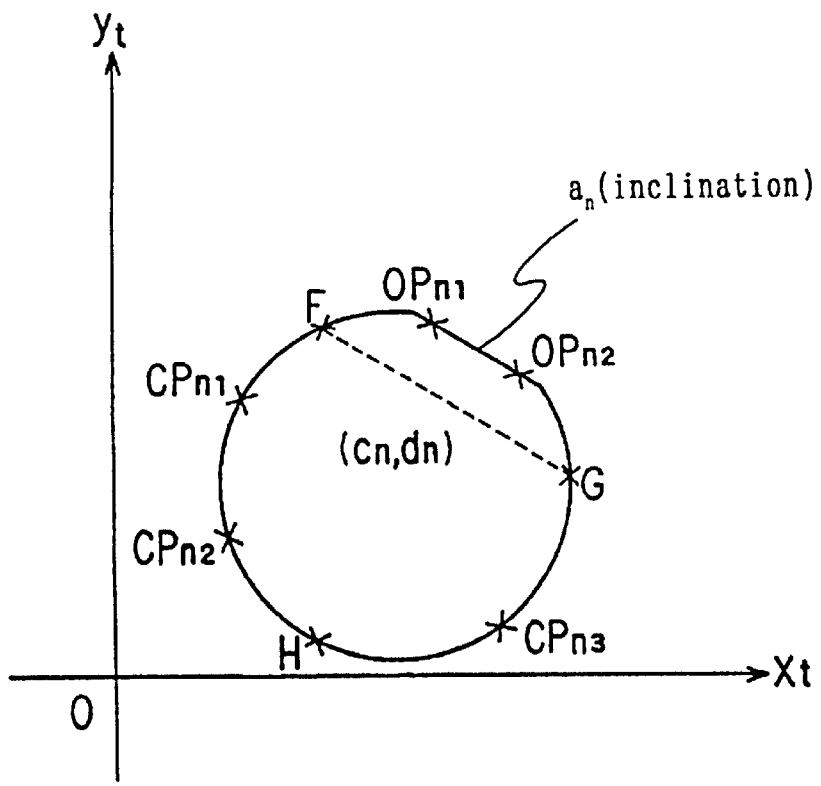
FIG. 2 is a view illustrating examples of sampling points used for defining a common coordinate system when a wafer having an orientation flat has been placed on a stage as the sample.

In order to select the sampling points from among the predetermined portions of the circular arc portion of the wafer which reflect the outer peripheral configuration thereof, since the diameter of the wafer in approximation is made previously known such as, for example, 6 inches or 8 inches and since the dimension of the cut-off portion of the wafer as seen in the orientation flat thereof in approximation is made previously known, the following method can be adopted for example. That is, as illustrated in FIG. 2, a straight line which is spaced by a predetermined distance from the orientation flat and parallel therewith is defined and the following three points are sampled, namely two points F and G of intersection between this parallel line and the outer periphery of the wafer and a point H at a position where a parallel line with the orientation flat is tangent to the circular arc portion, whereby equidistant three points can be sampled.

Although in each of the above-mentioned embodiments two points from the straight line portion of the orientation flat and three points from the circular arc portion were selected as the sampling points, the precision further increases by increasing the number of these sampling points. In this case, when, for example, the inclination or center coordinates are determined, they can be approached to a true inclination or center coordinates by averaging the inclinations and center coordinates determined from two or three points by use of least square.

In this case, in a case where four or five points on the circular arc are used as sampling points, the sampling points may be selected so as to define a square or regular pentagon and the center coordinates are determined from its three points. Alternatively, the positions of three points of an equilateral triangle are measured and these three points are totally rotated as they stand whereby three points at different positions are further measured to thereby determine the center coordinates from the resulting values. Thereby, the center coordinates are averaged by least square, thus the precision further increases.

[Embodiment No. 3]

Figure 5:
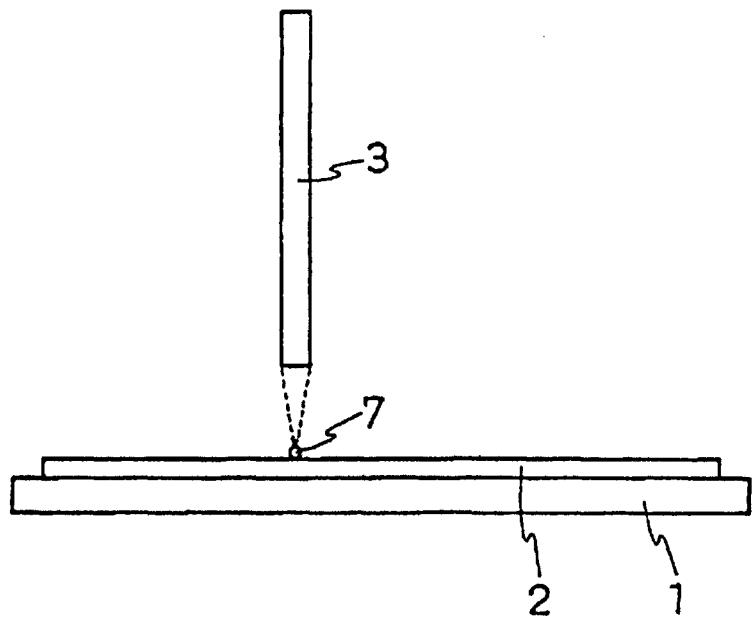
FIG. 5 is a view illustrating the construction of an embodiment of an analyzing method and analyzing apparatus of the present invention wherein a metallurgical microscope is used as the analyzing apparatus.

FIG. 5 is a view illustrating a fundamental construction of an actuator-equipped metallurgical microscope as an example of a metallurgical microscope with coordinate-linking function used in an embodiment of an observing method for observing a minute foreign substance according to the present invention. Although the apparatus construction is the same as the fundamental construction of a conventional actuator-equipped metallurgical microscope, the metallurgical microscope of the present invention is provided with the above-mentioned means for setting a common coordinate system.

First, in accordance with the procedures stated in the embodiment no. 1, a coordinate system based on configurations of a wafer is defined with respect to a particle examination equipment produced by Tencor Corporation and having an equipment name of (Surfscan 6200) and an actuator-equipped metallurgical microscope to thereby perform linkage between the equipment coordinates and apparatus coordinates of the both equipment and apparatus. Then, the amount of divergence which occurred therefrom was examined using a plurality of wafers each having a grated pattern. As a result, in the x-y coordinate display, it was proved that only the amount of divergence of approximately ($\pm 150\,\mu$m, $\pm 150\,\mu$m) or less occurred in respect of the origin position or center position and a given point definable therein, whereby it was understood that there was an appreciable level of improvement effect.

For this reason, observation attempted to be made on a minute foreign substance having a size of about 0.4 $\mu$m or so which existed on a silicon wafer for use in manufacture of a semiconductor device. As a result, even when the metallurgical microscope had 200 magnifications (the ocular lens was set to 20 magnifications and the objective lens was set to fixed 10 magnifications), the minute foreign substance could be moved to within the range of the view field, with the result that a minute foreign substance having a size of 0.4 $\mu$m or so which was conventionally impossible to observe could be observed reliably by means of the microscope.

[Embodiment No. 4]

Also, with respect to a particle examination equipment produced by Tencor Corporation and having an equipment name of (Surfscan 6200) and an actuator-equipped metallurgical microscope, in accordance with the procedures stated in the embodiment no. 2, two sets of sampling points were selected at the positions of equilateral triangles and least square was applied to prepare a coordinate system commonly available between the both equipment and apparatus to thereby perform linkage between the equipment coordinates and apparatus coordinates of the both equipment and apparatus. Then, the amount of divergence which occurred therefrom was examined using a plurality of wafers each having a grated pattern. As a result, in the x-y coordinate display, it was proved that only the amount of divergence of approximately ($\pm 80\,\mu$m, $\pm 80\,\mu$m) or less occurred in respect of the origin position or center position and a given point definable therein, whereby it was understood that there was an appreciable level of improvement effect.

For this reason, observation attempted to be made on a minute foreign substance having a size of about 0.3 $\mu$m or so which existed on a silicon wafer for use in manufacture of a semiconductor device. As a result, even when the metallurgical microscope had 400 magnifications (the ocular lens was set to 20 magnifications and the objective lens was set to fixed 20 magnifications), the minute foreign substance could be moved to within the range of the view field, with the result that a minute foreign substance having a size of 0.3 $\mu$m or so which was conventionally impossible to observe could be observed reliably by means of the microscope.

[Embodiment No. 5]

In this embodiment, as an analyzing apparatus, there is used in place of the metallurgical microscope 3 of the embodiment no. 4 a conventional scanning laser microscope provided with the above-mentioned means for setting a common coordinate system therein such as, for example, an apparatus put on sale from Nikon Corporation and having an apparatus name of RCM 8000. Therefore, the other construction is completely the same as that illustrated in FIG. 5 and the method for coordinate linkage is also completely the same as that adoped in the embodiment no. 4.

For this reason, observation attempted to be made on a minute foreign substance having a size of about 0.2 µm or so which existed on a silicon wafer for use in manufacture of a semiconductor device. Ultraviolet rays were used for observation and observation was made of each minute foreign substance 7. As a result, it was possible to observe the surface of the minute foreign substances 7 having a size of 0.2 µm or so and it was also possible to find out dark spots concerning the minute foreign substances 7 having a size of 0.2 µm or less.

This embodiment is characterized in that surface observation is possible with no breakage and in the atmosphere, and, when it is used in a manufacturing process for manufacturing a semiconductor device or liquid crystal display device, is effective particularly for analysis of foreign substances in process steps which succeed the film forming step.

[Embodiment No. 6]

In this embodiment, as an analyzing apparatus, there is used in place of the metallurgical microscope 3 of the embodiment no. 4 a conventional micro FTIR such as, for example, an apparatus put on sale from Japan Electron Optics Laboratory Co. Ltd. and having an apparatus name of micro infrared-ray unit IR-MAU 110 loaded JIR-5500. This apparatus is similarly provided with the above-mentioned means for setting a common coordinate system therein (note that this apparatus is loaded with a metallurgical microscope). Therefore, the other construction is completely the same as that illustrated in FIG. 5 and the method for coordinate linkage is also completely the same as that adoped in the embodiment no. 4. Thus, it was possible to set minute foreign substances having a size of up to 0.2 µm For this reason, observation attempted to be made on a minute foreign substance having a size of about 0.2 µm or more which existed on a silicon wafer for use in manufacture of a semiconductor device. As a result, since the wavelength of infrared rays is long, an IR spectrum was not obtained from minute foreign substances having a size of 0.2 µm or so. However, when minute foreign substances larger in size were gradually moved to within the view field thereof, an IR spectrum which is specific for organic material was obtained from several foreign substances having a size of 3 µm or more, and it was proved that generated causes of these substances were due to a failure to perform sufficient resist elimination. This analysis is effective particularly when used in process steps succeeding a resist coating step in the manufacturing process for manufacturing a semiconductor device or liquid crystal display device.

[Embodiment No. 7]

In this embodiment, as an analyzing apparatus, there is used in place of the metallurgical microscope 3 of the embodiment no. 4 a conventional Microscopic Raman such as, for example, an apparatus put on sale from Jasco Corporation and having an apparatus name of NR-1800. This apparatus, for example, is similarly provided with the above-mentioned means for setting a common coordinate system therein (note that this apparatus is loaded with a metallurgical microscope). Therefore, the other construction is completely the same as that illustrated in FIG. 5 and the method for coordinate linkage is also completely the same as that adoped in the embodiment no. 4. Thus, it was possible to set minute foreign substances having a size of up to 0.2 µm.

For this reason, observation attempted to be made on a minute foreign substance having a size of about 0.2 µm or so which existed on a silicon wafer for use in manufacture of a semiconductor device. As a result, although no Raman spectrum was obtained from a minute foreign substance having a size of 0.2 µm or so, a Raman spectrum which is specific for inorganic material was obtained from several foreign substances having a size of 1 µm or more, and it was proved that generated causes of these substances were related to something during the film forming step. This analysis is effective particularly when used in process steps having relevancy to the film forming, etching, cleaning or the like in the manufacturing process for manufacturing a semiconductor device or liquid crystal display device.

[Embodiment No. 8]

In this embodiment, as an analyzing apparatus, there is used in place of the metallurgical microscope 3 of the embodiment no. 4 a conventional PL such as, for example, an apparatus put on sale from Jasco Corporation and having an apparatus name of 25 C type. This apparatus, for example, is similarly provided with the above-mentioned means for setting a common coordinate system therein (note that this apparatus is loaded with a metallurgical microscope). Therefore, the other construction is completely the same as that illustrated in FIG. 5 and the method for coordinate linkage is also completely the same as that adoped in the embodiment no. 4. Thus, it was possible to set minute foreign substances having a size of up to 0.2 µm.

For this reason, observation attempted to be made on a minute foreign substance having a size of about 0.2 µm or more which existed on a silicon wafer for use in manufacture of a semiconductor device. As a result, although no fluorescent spectrum was obtained from a minute foreign substance having a size of 0.2 µm or so, a fluorescent spectrum which is specific for inorganic or cystallinge material was obtained from several foreign substances having a size of 3 µm or more, and it was proved that generated causes of these substances were related to the film formation, etching and heat treatment. This analysis is effective particularly when used in process steps having relevancy to the film formation, etching and heat treatment in the manufacturing process for manufacturing a semiconductor device or liquid crystal display device.

[Embodiment No. 9]

In this embodiment, as an analyzing apparatus, there is used in place of the metallurgical microscope 3 of. the embodiment no. 4 a conventional fluorescence spectrophotometer such as, for example, an apparatus put on sale from Hitachi Limited and having an apparatus name of F-2000. This apparatus, for example, is similarly provided with the above-mentioned means for setting a common coordinate system therein (note that this apparatus is loaded with a metallurgical microscope). Therefore, the other construction is completely the same as that illustrated in FIG. 5 and the method for coordinate linkage is also completely the same as that adoped in the embodiment no. 4. Thus, it was possible to set minute foreign substances having a size of up to 0.2 µm.

For this reason, observation attempted to be made on a minute foreign substance having a size of about 0.2 µm or more which existed on a silicon wafer for use in manufacture of a semiconductor device. As a result, although no fluorescent spectrum was obtained from a minute foreign substance having a size of 0.2 µm or so, a fluorescent spectrum which is specific for inorganic material was obtained from several foreign substances having a size of 2 µm or more, and it was proved that generated causes of these substances were related to the film formation, etching and cleaning. This analysis is effective particularly when used in process steps having relevancy to the film formation, etching and cleaning in the manufacturing process for manufacturing a semiconductor device or liquid crystal display device.

[Embodiment No. 10]

Figure 6:
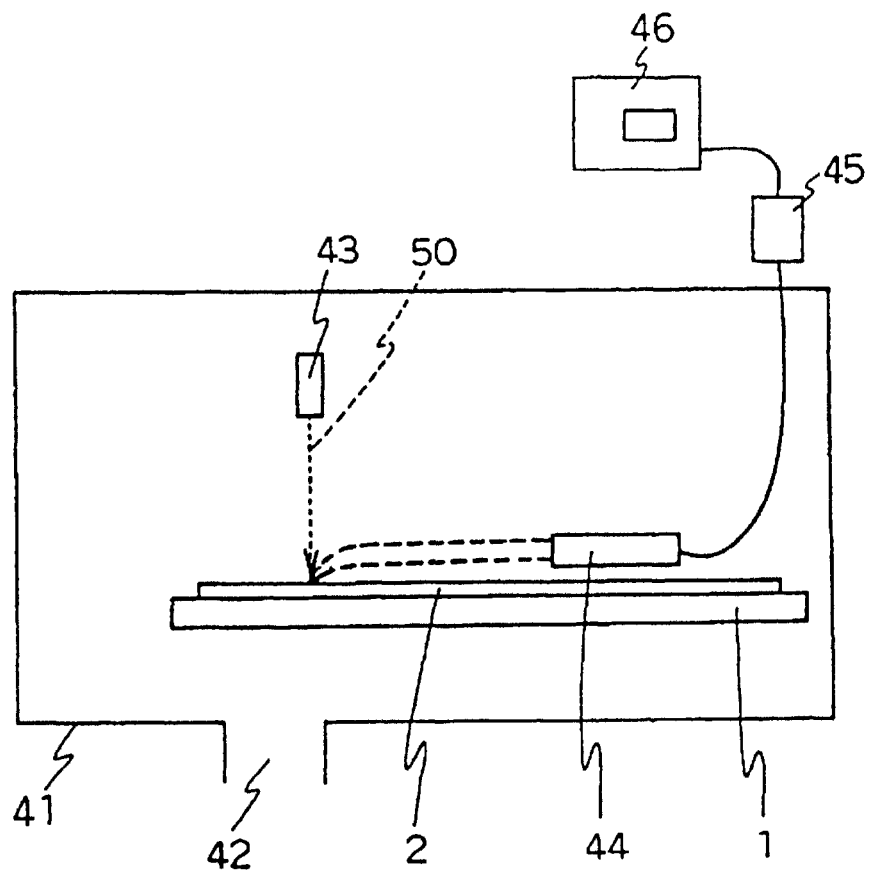
FIG. 6 is a view illustrating the construction of an embodiment of the analyzing method and analyzing apparatus of the present invention wherein a length measuring SEM is used as the analyzing apparatus.

FIG. 6 is a view illustrating the fundamental construction of another embodiment of the analyzing method for analyzing minute foreign substance according to the present invention. The difference between this embodiment and the embodiment no. 4 is that in place of the metallurgical microscope 3 used in FIG. 5 there is used an apparatus such as, for example, a length measuring SEM put on sale from Hitachi Limited and having an apparatus name of S-7000. This embodiment is the same as the embodiment no. 4, for example, in that the above-mentioned means for setting a common coordinate system is provided (provided, however, that the x-y stage used differs from that in the embodiment no. 4).

In this embodiment, as illustrated in FIG. 6, the analyzing apparatus is composed of an electron gun unit 43 equipped with an electron gun for applying scanning electron beams 50 onto a silicon wafer 2 and an electron lens and a secondary electron detector 44 for converting secondary electrons generated from the silicon wafer 2 to electric signals, the signals obtained from the secondary electron detector 44 being supplied to amplifying and controlling unit 45 for amplifying and controlling electric signals and displayed by an CRT 46 for outputting a secondary electron image. Reference numeral 41 represents a chamber for maintaining these units or devices under vacuum, which chamber is evacuated and maintained in vacuum. Using this length measuring SEM, the minute foreign substance 7 existing on the silicon wafer 2 can be inspected according to completely the same procedures as those used in the embodiment no. 4. That is, a coordinate system based on configurations of a wafer is defined on the stage of the length measuring SEM in accordance with the procedures shown in the embodiments nos. 1 and 2.

As in the case of the embodiment no. 4, the amount of divergence occurring from the coordinate linkage was examined using a plurality of wafers each formed with a grated pattern and it was proved that in the x-y coordinate display only the amount of divergence of approximately (±30 $\mu$m, ±30 $\mu$m) occurred in respect to the origin position or center position or a given point definable therein, thus it was found out that an appreciable level of improvement effect was obtained.

For this reason, observation attempted to be made on minute foreign substances having a size of 0.1 $\mu$ or so which existed on a silicon wafer used in the manufacturing process for manufacturing a semiconductor device. According to this embodiment, in regard to the minute foreign substance 7, this minute foreign substance could be easily found out within the view field (the magnification was set to 300-magnification) of the SEM, thus a clear SEM image could be obtained. The minute foreign substance 7 was varying such as protruding (convex) ones or depressed (concave) ones and its configuration could be grasped. The analysis of this embodiment is effective particularly for all of the process steps such as film formation, etching, cleaning, exposure, ion implantation, diffusion and heat treatment in the manufacturing process for manufacturing a semiconductor device or liquid crystal display device.

[Embodiment No. 11]

Figure 7:
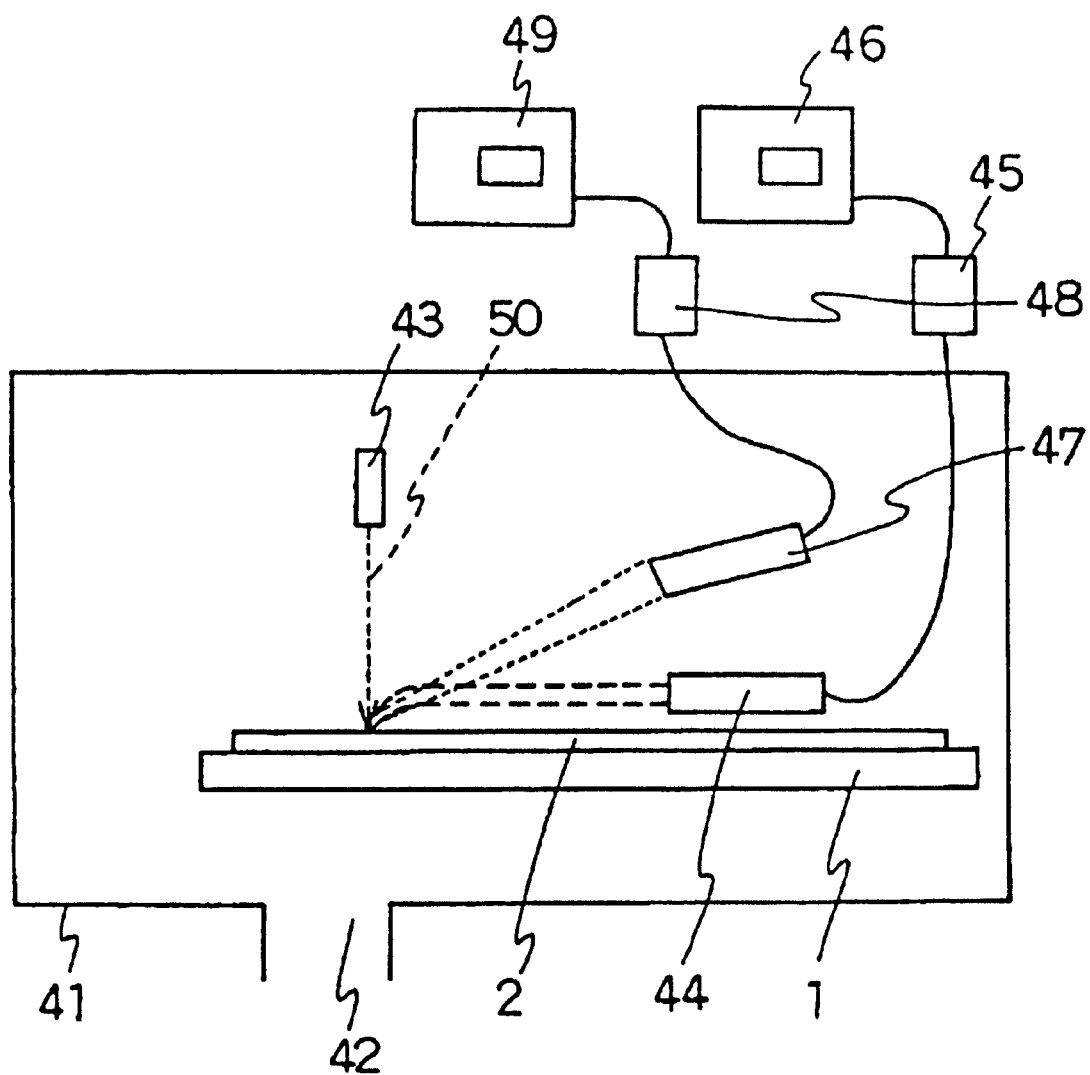
FIG. 7 is a view illustrating the construction of an embodiment of the analyzing method and analyzing apparatus of the present invention wherein an EPMA having the positioning function is used as the analyzing apparatus.

FIG. 7 is a view illustrating the fundamental construction of still another embodiment of the analyzing method for analyzing minute foreign substances according to the present invention. In this embodiment, an apparatus in which the SEM of the embodiment no. 10 is used has added thereto an X-ray detector 47, an amplifying/controlling unit 48 for amplifying and controlling electric signals supplied from the X-ray detector 47, and a CRT 49 for displaying an X-ray output. As a result of this, an EPMA is formed and the other parts construction is completely the same as that of the embodiment no. 10. Further, also, the coordinate linking method such as that wherein there is provided the means for setting a coordinate system based on the configurations of a wafer is completely the same as in the case of the embodiment no. 10. Using this embodiment, according to completely the same procedures as those used in the embodiment no. 10, observation was made on the minute foreign substance 7 existing on the surface of the same silicon wafer 2. As a result, elemental analysis could be made on the protruding foreign substances 7. It was proved that the minute foreign substances 7 were, for example, compounds of W, Cu, Fe, C, S, O and Cl. However, when performing detailed elemental analyses of the minute foreign substances 7 having a size of 0.3 $\mu$m or less, a significantly long period of time was needed.

The analysis of this embodiment is effective particularly for all of the process steps such as film formation, etching, cleaning, exposure, ion implantation, diffusion and heat treatment in the manufacturing process for manufacturing a semiconductor device or liquid crystal display device.

[Embodiment No. 12]

In this embodiment, as an analyzing apparatus, an AES is used in place of the EPMA of the embodiment no. 11. The other construction is completely the same as the construction shown in FIG. 7 and the means for performing coordinate linkage and the operating method therefor are also completely the same as that in the case of the embodiment no. 10. As the AES, there can be used, for example, a PHI-670 produced by Perkin Elmer Corporation. The minute foreign substance 7 existing on the surface of the silicon wafer 2 was analyzed by use thereof in the same manner as in the case of each of the above-mentioned embodiments. As a result, elemental analysis could be performed on the protruding minute foreign substances 7. By the composition of the minute foreign substances 7, it was possible to discriminate compounds of W, Cu, Fe, C, S, O and Cl and particularize the dust generation sources and take countermeasures thereagainst. The analysis of this embodiment is effective particularly for all of the process steps such as film formation, etching, cleaning, exposure, ion implantation, diffusion and heat treatment in the manufacturing process for manufacturing a semiconductor device or liquid crystal display device.

[Embodiment No. 13]

In this embodiment, as an analyzing apparatus, an EELS is used in place of the EPMA of the embodiment no. 11. The other construction is completely the same as the construction shown in FIG. 7 and the means for performing coordinate linkage and the operating method therefor are also completely the same as that in the case of the embodiment no. 10. As the EELS, there can be used, for example, a PHI-660 produced by Perkin Elmer Corporation. The minute foreign substance 7 existing on the surface of the silicon wafer 2 was examined by use thereof in the same manner as in the case of each of the above-mentioned embodiments. As a result, compound analysis could be performed on the protruding minute foreign substances 7, with the result that a state of chemical bondage thereof was clarified. It was thus possible to particularize the dust generation sources and take countermeasures thereagainst. The analysis of this embodiment is effective particularly for the film forming, etching and exposure steps in the manufacturing process for manufacturing a semiconductor device or liquid crystal display device.

[Embodiment No. 14]

Figure 8:
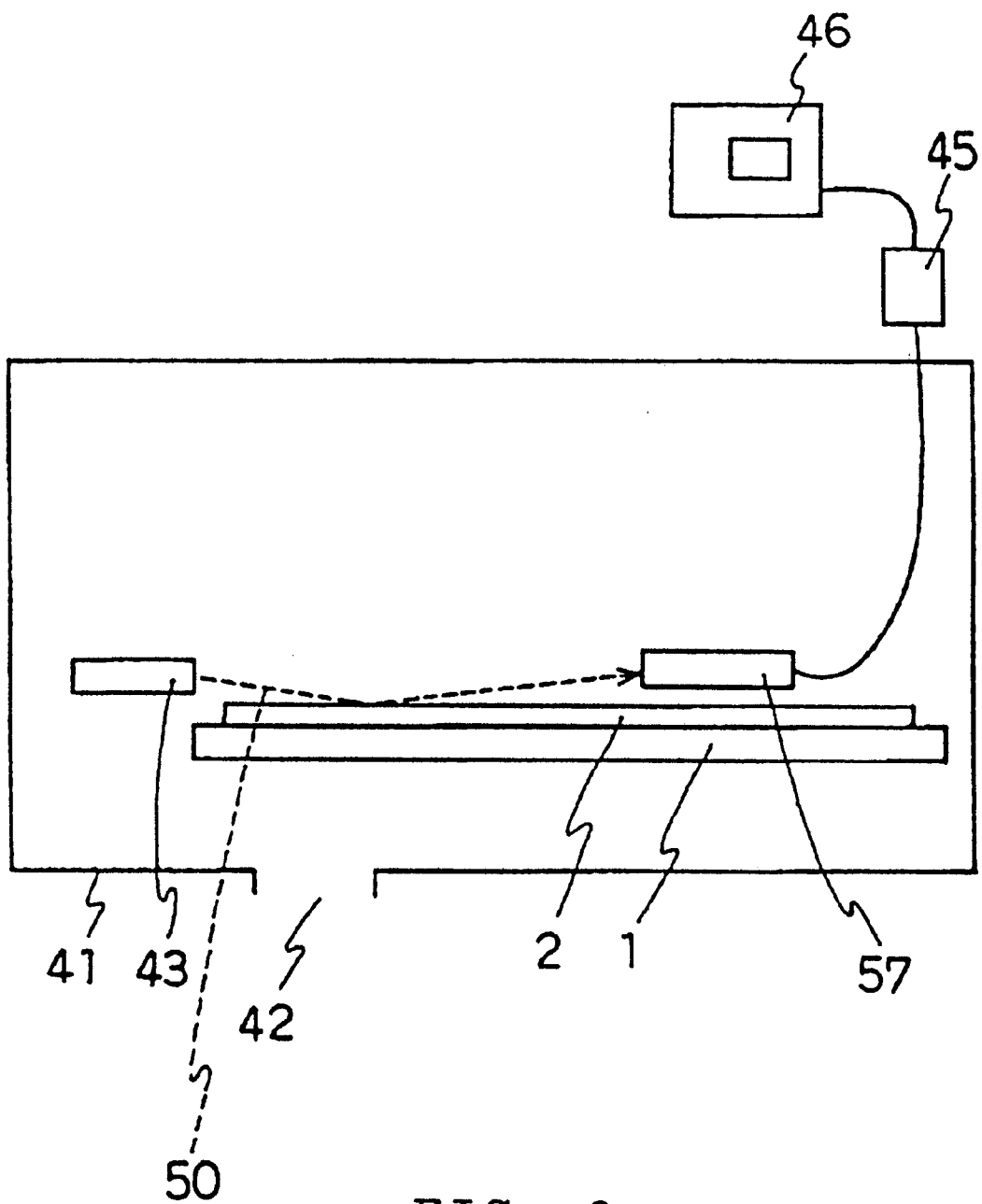
FIG. 8 is a view illustrating the construction of an embodiment of the analyzing method and analyzing apparatus of the present invention wherein an RHEED is used as the analyzing apparatus.
Figure 9:
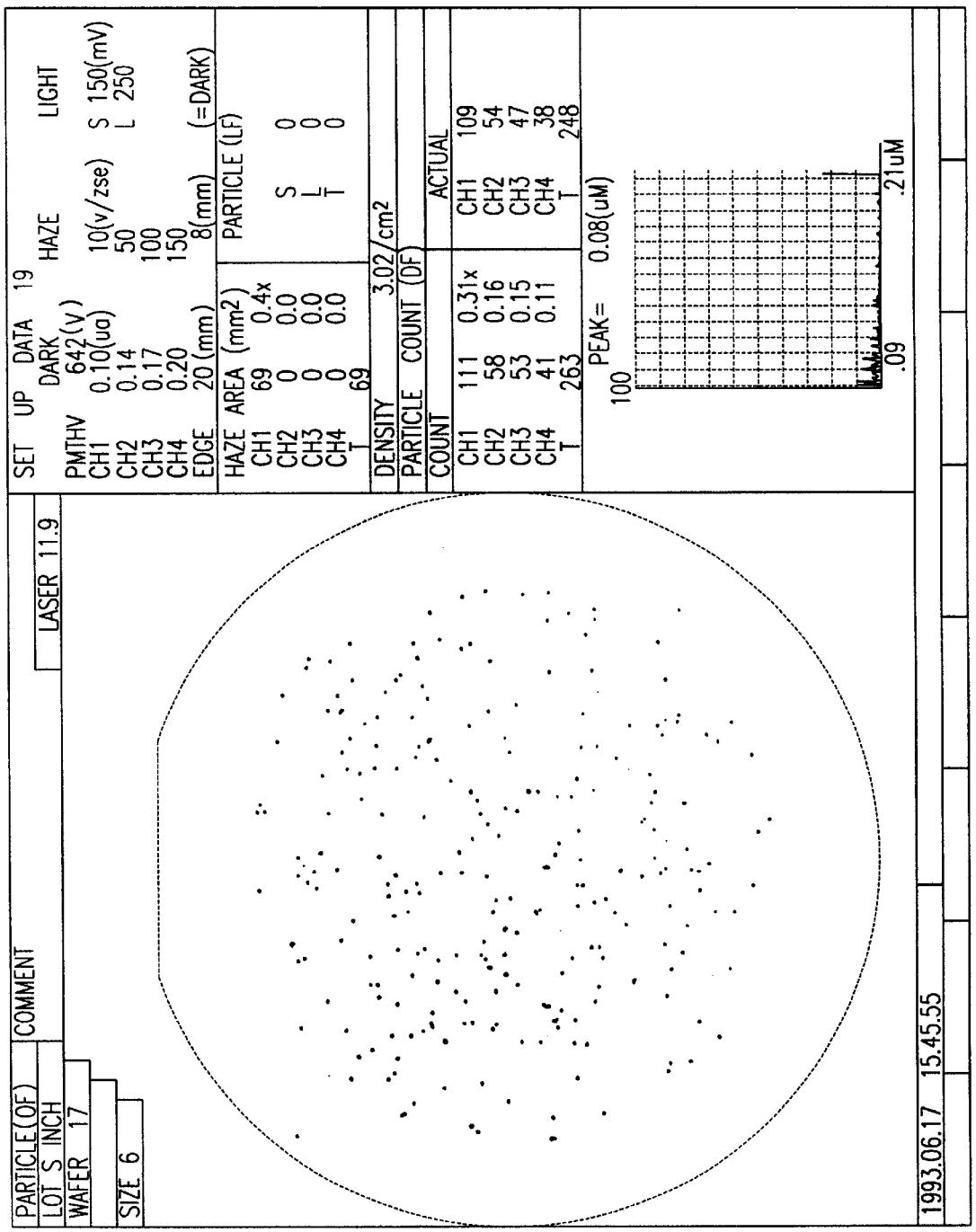
FIG. 9 illustrates an example of a result of measurement made on a foreign substance on a silicon wafer by use of a particle examination equipment.
Figure 10A:
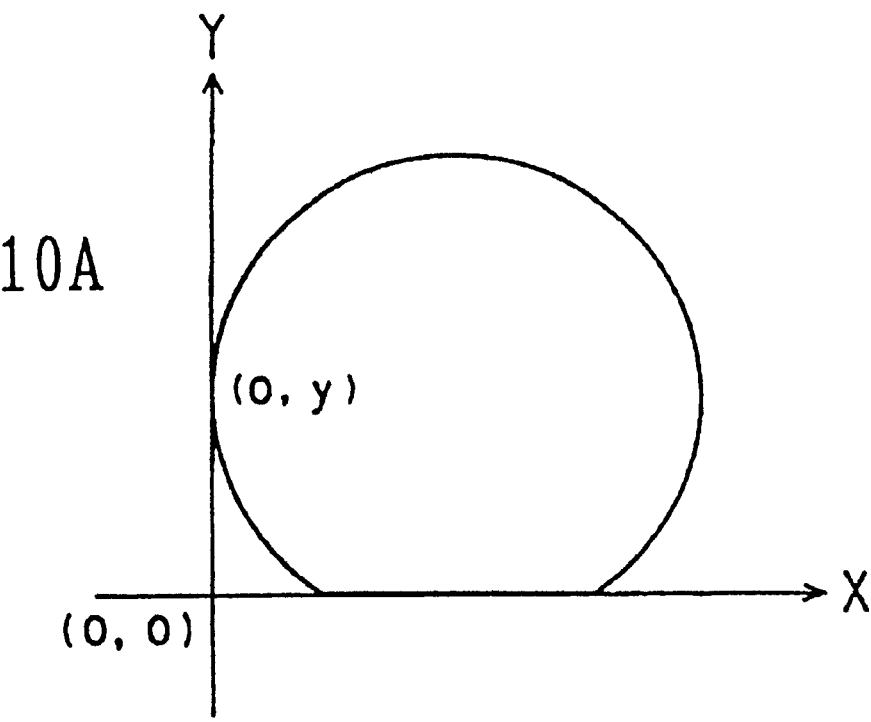
FIG. 10 is a view illustrating examples of defining equipment and apparatus coordinates adopted in conventional particle examination equipment and analyzing apparatus.
Figure 10B:
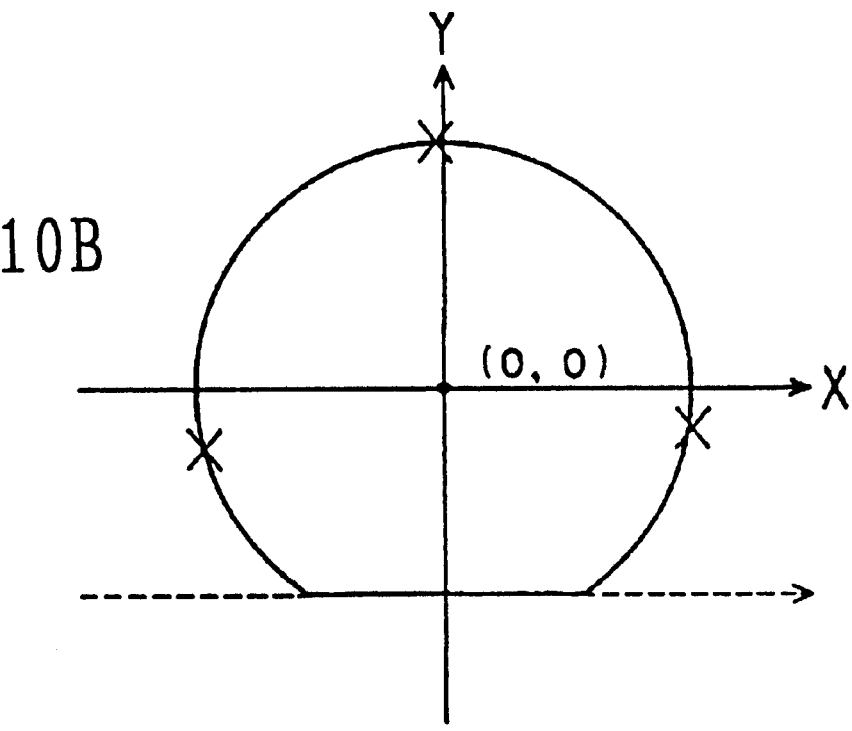

FIG. 8 is a view illustrating the fundamental construction of an RHEED used in a further embodiment of the minute foreign substance analyzing method according to the present invention. This embodiment differs from the embodiment no. 10 in that the electron gun unit 43 used in the embodiment no. 10 is inclined at approximately the same. angle as that at which the secondary electron detector 44 is inclined with respect to the silicon wafer 2 and thereby installed at a position permitting electron beams 50 to be irradiated onto the surface of the silicon wafer 2 in such a manner as to be approximately in parallel therewith, and in that a CCD camera 57 for obtaining diffraction spots of electron beams diffracted at the surface of the silicon wafer 2 is installed in place of the secondary electron detector 44. It is the same as the embodiment no. 10 in the other respects.

Using this, the minute foreign substance 7 existing on the surface of the silicon wafer 2 was examined as in each of the above-mentioned embodiments. As a result, concerning several ones of the minute foreign substances 7, diffraction spots were obtained and it was proved that these substances were crystalline materials and, in a case where these substances were crystalline materials such as whisker, the growth thereof could be suppressed. When used after the performance of film forming and heat treating steps in the manufacturing process for manufacturing a semiconductor device or liquid crystal display device, the analysis of this embodiment is effective for obtaining the suppressing effect of abnormal growth of the crystals and for selecting the conditions therefor.

[Embodiment No. 15]

In this embodiment, as an analyzing apparatus, there is used in place of the EPMA of the embodiment no. 11 an SIMS, namely an apparatus wherein the electron gun unit 43 of the embodiment no. 10 is replaced by an ion gun unit equipped with an ion gun and a condenser lens and, for the purpose of irradiating scanning ion beams in place of the electron beams 50 onto the surface of the silicon wafer 2 and separating and detecting secondary ions generated from the surface of the silicon wafer 2 in place of the secondary electron detector 44, a mass analyzing unit comprising a double-focusing mass spectrometer or quadrupole mass spectrometer is used. The other construction is completely the same as that illustrated in FIG. 5, and the means for performing coordinate linkage and the operating method therefor are also the same as in the embodiment no. 11.

As the SIMS, for example IMS-5F produced by CAMECA can be used.

Using this, the minute foreign substance 7 existing on the surface of the silicon wafer 2 was examined as in each of the above-mentioned embodiments. As a result, concerning the protruding (convex) minute foreign substances 7, composition analysis could be performed and the generated causes of the minute foreign substances were proved and it was also proved that adverse effect thereof existed upon a decrease in the yield due to deterioration of electrical characteristics resulting from diffusion of metals from the foreign substances. This analysis is effective particularly for use in the film forming, etching, cleaning and heat treating steps in the manufacturing process for manufacturing a semiconductor device or liquid crystal display device.

[Embodiment No. 16]

In this embodiment, a TOF-SIMS is used in place of the SIMS of the embodiment no. 15, namely a mass analyzing unit using a time of flight-mass spectrometer is used in place of a mass analyzing unit such as a double focusing mass spectrometer or quadrupole mass spectrometer is used. The other construction is completely the same as that illustrated in FIG. 5, and the means for performing coordinate linkage and the operating method therefor are also the same as in the embodiment no. 11.

According to this embodiment, analysis can be performed on the chemical structure of foreign substances by analyzing fragments from these foreign substances. Unlike the embodiment no. 15, this embodiment has a merit in that it is possible to make analysis of high molecular material existing on the outermost surface of foreign substances. Accordingly, this embodiment is effective particularly for analysis of foreign substances containing organic materials or the like.

[Embodiment No. 17]

In this embodiment, a PIXE is used in place of the SIMS of the embodiment no. 15, and has added to the construction of the embodiment no. 15 an X-ray detector, an amplifying and controlling unit for amplifying and controlling electrical signals supplied from the X-ray detector, and a CRT for outputting an X-ray image.

According to this embodiment, composition analysis of each foreign substance can be made and, particularly, the analysis of this embodiment suits elemental analysis with high sensitivity and precision. Accordingly, the analysis of this embodiment is effective particularly for analysis of an ultra-minute particle having a size of 0.1 $\mu$m or less.

[Embodiment No. 18]

In this embodiment, as an analyzing apparatus, there is used in place of the X-ray detector of the embodiment no. 10 an FIB which comprises in place of the electron gun unit 43 of the embodiment no. 10 an ion gun unit equipped with an ion gun and a condenser lens to thereby irradiate in place of the electron beams 50 scanning ion beams onto the surface of the silicon wafer 2 and thereby enable performance of the elimination processing for eliminating unnecessary foreign substances. The other construction is completely the same as that illustrated in FIG. 6, and the means for performing coordinate linkage and the operating method therefor are also the same as in the embodiment no. 10.

According to this embodiment, there is the advantage that minute foreign substances can be observed, unnecessary foreign substances can be eliminated, and immediate repair can be performed. Accordingly, this embodiment is effective particularly for increasing the yield by repair of the inconveniences resulting from foreign substances.

[Embodiment No. 19]

In this embodiment, an XPS using soft X rays such as AlK$\alpha$ or MgK$\alpha$ is used in place of the electron gun unit 43 of the embodiment no. 11. The other construction is completely the same as that illustrated in FIG. 7, and the method for performing coordinate linkage and the like are also the same as in the embodiment no. 11.

According to this embodiment, since chemical bond analysis can be made on protruding foreign substances 7 and in this embodiment in particular soft X-ray beams are used, there is the effect that the sample is less damaged. Accordingly, this embodiment is effective particularly for performing analysis at a place several tens of angstroms or so from the outermost surface of a foreign substance without damaging it.

[Embodiment No. 20]

In this embodiment, a USP-using ultraviolet ray beams which form ultraviolet rays generated from a high pressure mercury lamp into beam configurations is used in place of the electron gun unit 43 of the embodiment no. 11. The other construction is completely the same as that illustrated in FIG. 7, and the means for performing coordinate linkage, the method therefor and the like are also the same as in the embodiment no. 11.

According to this embodiment, also, since composition analysis can be made on protruding foreign substances 7 and in this embodiment in particular ultraviolet ray beams are used, there is the effect that the sample is less. damaged. Accordingly, this embodiment is effective particularly for performing analysis at a place several tens of angstroms or so from the outermost surface of a foreign substance without damaging it.

[Embodiment No. 21]

In this embodiment, as an analyzing apparatus, a probe microscope SPA 350 (an AFM probe was used as the probe) produced by Seiko Industrial Co. Ltd., for example, is used in place of the metallurgical microscope 3 of the embodiment no. 4. Therefore, the other construction is completely the same as that illustrated in FIG. 5, and the means for performing coordinate linkage and the method therefor are also completely the same as in the embodiment no. 4. This embodiment is characterized in that the surface observation is possible in the atmospheric air.

For this reason, observation attempted to be made on minute foreign substances having a size of 0.1 $\mu$ or so which existed on a silicon wafer used in the manufacturing process for manufacturing a semiconductor device. According to this embodiment, in regard to the minute foreign substance 7, this minute foreign substance could be easily found out within the scanning range (the scanning range was 80 $\mu$m or less) of the AFM, thus a clear AFM image could be obtained. The minute foreign substance 7 was varying such as protruding ones or depressed ones and the configuration could be grasped. The analysis of this embodiment is effective particularly for all of the process steps such as film formation, etching, cleaning, exposure, ion implantation, diffusion and heat treatment in the manufacturing process for manufacturing a semiconductor device or liquid crystal display device.

[Embodiment No. 22]

In this embodiment, as an analyzing apparatus, a probe microscope SPA 350 (an STM probe was used as the probe) produced by Seiko Industrial Co. Ltd., for example, is used in place of the metallurgical microscope 3 of the embodiment no. 4. Therefore, the other construction is completely the same as that illustrated in FIG. 5, and the means for performing coordinate linkage and the method therefor are also completely the same as in the embodiment no. 4. This embodiment is characterized in that the surface observation is possible in the atmospheric air.

For this reason, observation attempted to be made on minute foreign substances having a size of 0.1 $\mu$ or so which existed on a silicon wafer used in the manufacturing process for manufacturing a semiconductor device. According to this embodiment, in regard to the minute foreign substance 7, this minute foreign substance could be easily found out within the scanning range (the scanning range was 80 $\mu$m or less) of the STM, thus a clear STM image could be obtained. The minute foreign substance 7 was varying such as protruding (convex) ones or depressed (concave) ones and the configuration could be grasped. The analysis of this embodiment is effective particularly for all of the process steps such as film formation, etching, cleaning, exposure, ion implantation, diffusion and heat treatment in the manufacturing process for manufacturing a semiconductor device or liquid crystal display device.

[Embodiment No. 23]

In this embodiment, as an analyzing apparatus, a probe microscope SPA 350 (an MFM probe was used as the probe) produced by Seiko Industrial Co. Ltd., for example, is used in place of the metallurgical microscope 3 of the embodiment no. 4. Therefore, the other construction is completely the same as that illustrated in FIG. 5, and the means for performing coordinate linkage and the method therefor are also completely the same as in the embodiment no. 4. This embodiment is characterized in that the surface observation is possible in the atmospheric air.

For this reason, observation attempted to be made on minute foreign substances having a size of 0.1 $\mu$ or so which existed on a silicon wafer used in the manufacturing process for manufacturing a semiconductor device. According to this embodiment, in regard to the minute foreign substance 7, this minute foreign substance could be easily found out within the scanning range (the scanning range was 80 $\mu$m or less) of the MFM, thus a clear MFM image could be obtained. And the generated causes of foreign substances were proved. The analysis of this embodiment is effective particularly for film forming and ion implantation steps in the manufacturing process for manufacturing a semiconductor device or liquid crystal display device.

[Comparative Example No. 1]

Using a particle examination equipment produced by Tencor Corporation and having an equipment name of Surfscan 6200 and a length measuring SEM produced by Hitachi Limited and having an apparatus name of S-7000, direct linkage was performed between the equipment and apparatus coordinates of the both equipment and apparatus and the amount of divergence generated was examined using a plurality of wafers each having a grated pattern. As a result, in the x-y coordinate display, it was proved that an amount of divergence of ($\pm$150 $\mu$m, $\pm$150 $\mu$m) in approximation occurred in respect of the origin position or center position and a given point definable therein.

As explained above, according to the analyzing method of this embodiment, since the equipment coordinates of the particle examination equipment and the apparatus coordinates of the analyzing apparatus are linked through the intermediary of a common coordinate system based on the configurations of a sample, it is possible to greatly decrease the amount of the divergence which occurs when conventional linkage is performed between the equipment coordinates of the particle examination equipment and the apparatus coordinates of the analyzing apparatus. As a result, the place of a minute foreign substance detected by the particle examination equipment can be readily set reliably into the view field of the analyzing apparatus by operating the equipment and apparatus coordinates of the both equipment and apparatus respectively.

Accordingly, a minute foreign substance which was conventionally difficult to detect in the wide surface area of a sample can be also detected by increasing the magnification and this minute foreign substance can be set within the view field of the analyzing apparatus, whereby the minute foreign substance can be readily detected and, in addition, surface observation, composition analysis and the like can be selectively performed within only a range where the minute foreign substance exists. Therefore, it is possible to largely shorten the measuring period of time and perform quality evaluation of the sample earlier.

Also, according to the analyzing apparatus of the present invention, since means for setting a coordinate system based on the configurations of a sample and means for determining the correlation function between this coordinate system and the apparatus coordinates are provided, the minute foreign substance detected by the equipment coordinates of a particle examination equipment provided with the same means can be reliably set in a shorter period of time into the view field of the analyzing apparatus by the apparatus coordinates thereof.

Furthermore, since the above-mentioned means for setting the coordinate system based on the configurations of a sample is provided to each of the above-mentioned analyzing apparatuses, it is possible to use as the analyzing apparatus one conforming to the goal and thereby not only perform analysis of the surface configuration, elemental analysis, analysis of chemical and crystalline structures, etc. but also perform surface processing.

Also, by applying the analyzing method and/or analyzing apparatus of the present invention to the manufacturing process for manufacturing a semiconductor device or liquid crystal display device, it is possible to prevent exertion of foreign substances onto fine patterns thereof, thus a semiconductor device or liquid crystal display device having increased yield and reliability can be obtained.

What is claimed is:

1. An analyzing apparatus for analyzing minute foreign substances comprising:
    an analyzer which analyzes minute foreign substances at a predetermined position on a stage, the location set according to apparatus coordinates;
    a sample locations of whose minute foreign substance have been detected and stored according to sample coordinates by a particle examination device, the sample disposed on the stage;
    means for determining the inclination of at least one prescribed linear portion of the sample by use of apparatus coordinates of the analyzing apparatus;
    means for determining the coordinates of a center of the sample from sampling points on an outer periphery thereof by use of the apparatus coordinates;
    coordinate transformation means for converting between sample coordinates based on the inclination and center coordinates and the apparatus coordinates so that the analyzer analyzes the minute foreign substances on the sample by sequentially setting the predetermined position to the stored locations.

2. An analyzing apparatus as set forth in claim 1, wherein the means for determining the center coordinates is one which determines the center coordinates by calculation made on the assumption that the measured sampling points satisfy the equation of a circle.

3. An analyzing apparatus as set forth in claim 1, wherein the analyzer is one selected from the group consisting of a scanning electron microscope, a metallurgical microscope, a scanning laser microscope, a Microscopic infrared spectrometer for analysis of a chemical structure, a Microscopic Raman spectrometer, a photoluminescence spectral analyzer for making fluorescence spectral analysis, an electron probe micro-analyzer for making elemental analysis of a minute amount of surface elements, an Auger electron spectrometer, an electron energy-loss spectrometer, a secondary ion mass spectrometer, a time of flight-mass spectrometer, a particle induced-x-ray emission, a reflection high energy electron diffraction spectrometer for analysis of crystals, focused ion beam instruments for making surface process, an x-ray photoelectron spectrometer for making structural analysis, an ultraviolet photoelectron spectrometer for making composition analysis, a scanning probe microscope, an interatomic force microscope, a scanning tunnel microscope, and a magnetic force microscope.

4. An analyzing apparatus as set forth in claim 2, wherein the analyzer is one selected from the group consisting of a scanning electron microscope, a metallurgical microscope, a scanning laser microscope, a Microscopic infrared spectrometer for analysis of a chemical structure, a Microscopic Raman spectrometer, a photoluminescence spectral analyzer for making fluorescence spectral analysis, an electron probe micro-analyzer for making elemental analysis of a minute amount of surface elements, an Auger electron spectrometer, an electron energy-loss spectrometer, a secondary ion mass spectrometer, a time of flight-mass spectrometer, a particle induced-x-ray emission, a reflection high energy electron diffraction spectrometer for analysis of crystals, focused ion beam instruments for making surface process, an x-ray photoelectron spectrometer for making structural analysis, an ultraviolet photoelectron spectrometer for making composition analysis, a scanning probe microscope, an interatomic force microscope, a scanning tunnel microscope, and a magnetic force microscope.

5. A particle examination device for detecting locations of minute foreign substances on a sample comprising;
    means for determining the inclination of at least one prescribed linear portion of the sample by use of equipment coordinates of the particle examination device;
    means for determining the coordinates of a center of the sample from sampling points on an outer periphery thereof by use of equipment coordinates of the particle examination device;
    coordinate transformation means for converting between a sample coordinate system based on the inclination and center coordinates and the equipment coordinates of the particle examination device; and
    means for storing locations of minute foreign substances on the sample according to sample coordinates.

6. An analyzing apparatus for analyzing minute foreign substances comprising:
    a particle examination device for determining a position of a minute foreign substance on a sample to permit analysis of a composition of the minute foreign substance; and
    an analyzing apparatus having a coordinate stage for receiving the sample from the particle examination device and receiving a signal indicating the position of the minute foreign substance as determined by the particle examination device, wherein the signal indicates the position in device coordinates adopted by the particle examination device and the position is translated to apparatus coordinates adopted by the analyzing apparatus by use of a sample coordinate system based on a configuration of the sample.

7. An analyzing apparatus according to claim 6, wherein the coordinate system based on a configuration of the sample is determined by measuring the positions of predetermined sampling points on the sample representing an outer peripheral edge thereof.

8. An analyzing apparatus according to claim 6, wherein the sample is a substrate having straight side edges, and two prescribed side edges of the substrate are measured as a series of sampling points by the examination device and by the analyzing apparatus, and the coordinates of a center obtained from a point of intersection between vertical bisectors of two prescribed side edges of the substrate and an inclination of one of the prescribed side edges, relative to an x-y coordinate system of the examination device and the analyzing apparatus, are determined, whereby an x-y coordinate system wherein a direction of the inclination is set as an x coordinate or y coordinate axis and the coordinates of the center are set as those of the origin to create the sample coordinate system.

9. An analyzing apparatus according to claim 7, wherein the sample is a substrate having straight side edges, and two prescribed side edges of the substrate are measured as a series of sampling points by the examination device and by the analyzing apparatus, and the coordinates of a center obtained from a point of intersection between vertical bisectors of two prescribed side edges of the substrate and an inclination of one of the prescribed side edges, relative to an x-y coordinate system of the examination device and the analyzing apparatus, are determined, whereby an x-y coordinate system wherein a direction of the inclination is set as an x coordinate or y coordinate axis and the coordinates of the center are set as those of the origin to create the sample coordinate system.

10. An analyzing apparatus according to claim 6, wherein the analyzing apparatus is one selected from the group consisting of a scanning electron microscope, a metallurgical microscope, a scanning laser microscope, a microscopic infrared spectrometer for analysis of a chemical structure, a microscopic Raman spectrometer, a photoluminescence spectral analyzer for making fluorescence spectral analysis, an electron probe micro-analyzer for making elemental analysis of a minute amount of surface elements, an Auger electron spectrometer, an electron energy-loss spectrometer, a secondary ion mass spectrometer, a time of flight-mass spectrometer, a particle-induced x-ray emission, a reflection high energy electron diffraction spectrometer for analysis of crystals, focused ion beam instruments for making surface process, an x-ray photoelectron spectrometer for making structural analysis, an ultraviolet photoelectron spectrometer for making composition analysis, a scanning probe microscope, and a magnetic force microscope.

* * * * *